United States Patent [19]

Blizzard et al.

[11] Patent Number: 5,055,454
[45] Date of Patent: Oct. 8, 1991

[54] 13-EPI-AVERMECTIN DERIVATIVES USEFUL AS ANTIPARASITIC AGENTS

[75] Inventors: Timothy A. Blizzard, Rahway; Helmut Mrozik, Matawan, both of N.J.

[73] Assignee: Merck & Co., Inc., Rahway, N.J.

[21] Appl. No.: 429,920

[22] Filed: Oct. 30, 1989

[51] Int. Cl.$^5$ .................... A61K 31/70; C07D 315/00
[52] U.S. Cl. ...................................... 514/30; 514/450; 514/336; 549/264; 536/7.1; 546/268
[58] Field of Search .......................... 536/7.1; 549/264; 514/450, 30

[56] References Cited

U.S. PATENT DOCUMENTS

| | | | |
|---|---|---|---|
| 3,950,360 | 4/1976 | Aoki et al. | 549/264 |
| 4,171,314 | 10/1979 | Chabala et al. | 549/264 |
| 4,173,571 | 11/1979 | Chabala et al. | 549/264 |
| 4,310,519 | 1/1982 | Albers-Schonberg et al. | 536/7.1 |
| 4,587,247 | 5/1986 | Linn et al. | 549/264 |

FOREIGN PATENT DOCUMENTS 170006  2/1986  European Pat. Off. .
235085  9/1987  European Pat. Off. .
2166436  5/1986  United Kingdom .

OTHER PUBLICATIONS

Albers-Schonberg et al. (II), *J. Am Chem Soc.* 103, pp. 4216–4221 (1981).
Chabala et al. (III), *J. Med Chem.*, 23, pp. 1134–1136 (1980).
Mrozik et al., *J. Org. Chem.*, 47, pp. 489–494 (1982).
Carter et al., *J. Antibiotics*, 41, pp. 519–529 (1988).
Blizzard et al., *J. Org. Chem.*, 54, p. 1756 (1989).

*Primary Examiner*—C. Warren Ivy
*Assistant Examiner*—Amelia A. Owens
*Attorney, Agent, or Firm*—David L. Rose; Joseph F. DiPrima

[57] ABSTRACT

There are disclosed avermectin derivatives in which position 13 of the avermectins has been inverted from the normal (alpha) stereochemistry to the epimeric 13-beta stereochemistry. The synthetic 13-epi analogs are derived from the corresponding aglycones which in turn are prepared by chemical modification of naturally occurring avermectins. The compounds are active antiparasitic agents and compositions for that use are disclosed.

20 Claims, No Drawings

13-EPI-AVERMECTIN DERIVATIVES USEFUL AS ANTIPARASITIC AGENTS

BACKGROUND OF THE INVENTION

The avermectins (previously referred to as C-076 compounds) are a series of compounds produced by fermentation of avermectin producing strains of *Streptomyces avermitilis* and derivatives thereof. The morphological characteristics of the culture are completely described in U.S. Pat. No. 4,310,519. The production, isolation, and structure determination of the avermectins are fully described in Albers Schonberg et al *J. Am. Chem. Soc.* 1981, 103, 4216–4221 and references cited therein. The conversion of natural avermectin $B_1$ to 22,23-dihydro-avermectin $B_1$, the potent broad spectrum anthelminthic agent known as ivermectin, has also been described in the literature (Chabala et al *J. Med. Chem.* 1980, 23, 1134–1136). The naturally occurring avermectins and the instant derivatives thereof have a very high degree of anthelminthic and anti-parasitic activity.

The naturally occurring avermectins are a series of macrocyclic lactones which are substituted at position 13 with a disaccharide consisting of two oleandrose residues. The preparation and properties of synthetic avermectin aglycones in which the disaccharide moiety has been removed leaving a free hydroxyl group at position 13 have been described by Mrozik et al *J. Org. Chem.* 1982, 47, 489–492 and by Chabala et al *J. Med Chem.* 1980, 23, 1134–1136. The natural compounds have the following general structure:

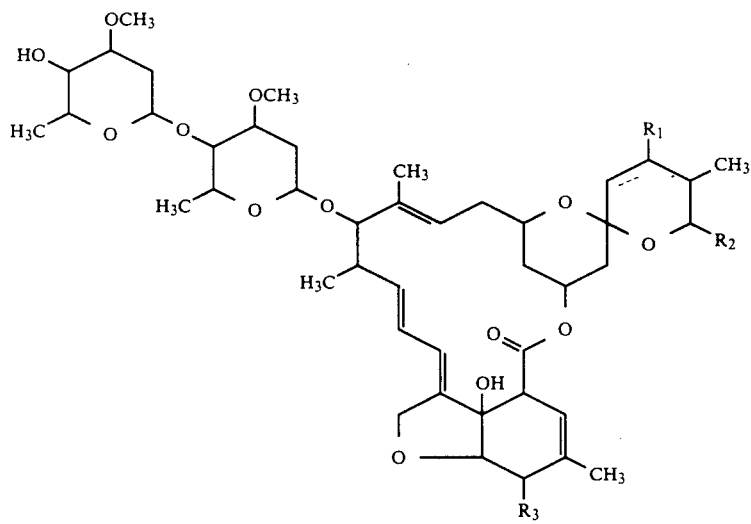

wherein the broken line indicates a single or double bond and;

$R_1$ is hydroxy and is present only when said broken line indicates a single bond;

$R_2$ is iso-propyl or sec-butyl; and $R_3$ is methoxy or hydroxy.

There are eight major natural avermectin compounds, designated $A_{1a}$, $A_{1b}$, $A_{2a}$, $A_{2b}$, $B_{1a}$, $B_{1b}$, $B_{2a}$ and $B_{2b}$. These designations are based on the structure of the individual compounds as shown in the following table (referring to the foregoing structural formula).

| Compound | broken line | $R_1$ | $R_2$ | $R_3$ |
|---|---|---|---|---|
| $A_{1a}$ | double bond | — | sec-butyl | —$OCH_3$ |
| $A_{1b}$ | double bond | — | iso-propyl | —$OCH_3$ |
| $A_{2a}$ | single bond | —OH | sec-butyl | —$OCH_3$ |
| $A_{2b}$ | single bond | —OH | iso-propyl | —$OCH_3$ |
| $B_{1a}$ | double bond | — | sec-butyl | —OH |
| $B_{1b}$ | double bond | — | iso-propyl | —OH |
| $B_{2a}$ | single bond | —OH | sec-butyl | —OH |
| $B_{2b}$ | single bond | —OH | iso-propyl | —OH |

The avermectins are generally isolated as mixtures of the a and b components (typically $\geq 80\%$ a and $\leq 20\%$ b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components is indicated by dropping the a or b from the designation of the compound. A mixture of avermectin $B_{1a}$ and avermectin $B_{1b}$ is thus referred to as avermectin $B_1$.

A related family of natural products is known as the milbemycins. The milbemycins have the same basic structure as the avermectins but have no substitution at position 13 and have a methyl or ethyl group at position 25 ($R_2$ =methyl or ethyl rather than isopropyl or sec-butyl as in the avermectins). The milbemycins and the fermentation conditions used to prepare them are described in U.S. Pat. No. 3,950,360. Closely related 13-deoxy-avermectin aglycones are prepared by chemical modification of the natural avermectins and have been described in U.S. Pat. Nos. 4,171,134 and 4,173,571.

Recently a number of related compounds have been described in European Patent Application EPO 170,006 and U.K. application 2,166,436 (see also Carter et al, *J. Antibiotics* 1988, 41, 519–529). These compounds are essentially 13-deoxy-avermectin aglycones in which the $R_2$ side chain contains a double bond and, in some cases, includes additional carbon atoms. Finally, a recent European Patent Application, EPO 235085, describes the conversion of various milbemycins to the 13-beta-glycosyloxy analogs.

SUMMARY OF THE INVENTION

This invention is concerned with certain avermectin derivatives in which the stereochemistry at position 13 is the opposite of the natural stereochemistry and the use of these derivatives as antiparasitic agents. Thus it is an object of this invention to describe these avermectin derivatives. A further object of this invention is to describe processes for the preparation of these compounds. A still further object is to describe the use of the instant compounds as antiparasitic agents in the treatment and prevention of parasitic diseases. A still further obJect is to describe compositions for the treatment of parasitic diseases which contain the novel compounds of this invention as the active ingredient thereof. Further obJects will become apparent from a reading of the following description.

DESCRIPTION OF THE INVENTION

The compounds of the instant invention are best realized in the following structure:

[Chemical structure diagram of avermectin derivative with labels OCH$_3$, $R_{4''}$, $R_{23}$, $R_{25}$, $R_5$, CH$_3$, H$_3$C, OH]

wherein the broken line indicates a single or double bond at the 22,23 position;

$R_{4''} = OH, NH_2$ NH-loweralkyl, NH-loweralkanoyl;
$R_5 = OH$, oxime, $OCH_3$;
$R_{23} = H$, OH, provided $R_{23}$ is not OH if the broken line indicates a double bond; and
$R_{25} =$ loweralkyl.

In the instant invention "loweralkyl" is intended to include those alkyl groups of from 1 to 7 carbon atoms in either a straight or branched chain. Examples of such loweralkyl groups are methyl, ethyl, propyl, isopropyl, butyl, sec-butyl, pentyl, hexyl, heptyl, and the like.

The term "loweralkanoyl" is intended to include those alkanoyl groups of from 1 to 7 carbon atoms in either a straight or branched chain. Examples of such loweralkanoyl groups are formyl, acetyl, propionyl, isopropionyl, butyryl, sec-butyryl, pentanoyl, hexanoyl, heptanoyl, and the like.

Preferred compounds of this invention are realized when:

$R_{4''} = OH, NH_2,$ NH-loweralkyl, NH-loweralkanoyl;
$R_5 = OH$, oxime, $OCH_3$;
$R_{23} = H$, OH;
$R_{25} =$ loweralkyl; and
the broken line indicates a single or double bond (provided that the broken line does not indicate a single bond if $R_{4''} = OH$ and $R_{23} = H$).

More preferred compounds of this invention are realized when:

$R_{4''} = OH, NH_2,$ NH-loweralkanoyl;
$R_5 = OH$;
$R_{23} = H$, OH;
$R_{25} =$ isopropyl or sec-butyl; and the broken line indicates a single or double bond.

Still more preferred compounds of this invention are realized when:

$R_{4''} = OH$, NH-loweralkanoyl;
$R_{23} = H$, OH; and
the broken line indicates a single or double bond.

The most preferred compounds of this invention are realized when:

$R_{4''} = OH,$ *NH-acetyl*;
$R_{23} = H$, OH,
and the broken line indicates a single or double bond.

Examples of the preferred compounds of this invention are as follows:

13-epi- avermectin B$_1$
1 -epi-avermectin B$_2$
13-epi-avermectin A$_1$
13-epi-avermectin A$_2$
4''-deoxy-4''amino 13-epi-avermectin B$_1$
4''-epi-amino-4''deoxy 13-epi-avermectin B$_1$
4''-amino 4''-deoxy-13-epi-22,23-dihydro-avermectin B$_1$
4''-epi-amino-4''-deoxy-13-epi-22,23 dihydro-avermectin B$_1$
4''-amino-4''-deoxy-13-epi-avermectin B$_2$
4''-epi-amino-4''-deoxy-13-epi avermectin B$_2$
4''-methylamino-4''-deoxy-13-epi avermectin B$_2$
4''-epi-methylamino-4''-deoxy-13-epi-avermectin B$_1$
4''-methylamino-4''-deoxy-13-epi-22,23-dihydro-avermectin B$_1$
4''-epi-methylamino-4''-deoxy-13-epi-22,23dihydro-avermectin B$_1$
4'''-methylamin-4''-deoxy-13-epi-avermectin B$_2$
4'''-epi-methylamino-4''-deoxy-13-epi-avermectin B$_2$
4''-acetylamino-4''deoxy-13-epi-avermectin B$_1$
4''-epi-acetylamino-4''deoxy-13-epi-avermectin B$_1$
4''-acetylamino-4''deoxy-13-epi-22,23-dihydro-avermectin B$_1$
4''-epi-acetylamino-4''deoxy-13-epi-22,23-dihydro-avermectic B$_1$
4''-acetylamino-4''deoxy-13-epi-avermectic B$_2$
4''-acetylamino-4''deoxy-13-epi-avermectin B$_2$
13-epi-avermectic B1 5-oxime
13-epi-avermectin B2 5-oxime

PREPARATION OF STARTING MATERIALS

The starting materials for this invention are disclosed in Albers-Schonberg et al. *J Am. Chem. Soc.* 1981, 103, 4216–4221 and references cited therein (naturally occurring avermectins), Chabala et al *J. Med. Chem.* 1980, 23, 1134–1135 (22, 23-dihydro-avermectin B$_1$ (ivermectin), and 22,23-dihydro-avermectin B$_1$-aglycone), Mrozic et al *J. Org. Chem.* 1982, 47, 489–492 (avermectin aglycones), Mrozik et al *J. Med. Chem.* 1989, 32, 375–381 (13-epi-avermectin aglycones), Linn et al U.S. Pat. No. 4,587,247, and Blizzard et al *J. Org. Chem.* 1989, 54, 1756 (avermectin disaccharide).

The novel compounds of this invention are prepared by the following procedures:

The instant compounds are prepared by attaching a disaccharide unit to a 13-epi-avermectin aglycone. Attachment of the disaccharide may be effected by a variety of glycosylation procedures such as reaction of the aglycone with a glycosyl fluoride or other halide in the presence of one or more salts of various metals such as silver, tin, mercury, copper and the like. An alternative procedure involves reaction of the aglycone with a glycosyl phenylsulfide or a glycosyl pyridylsulfide or a glycosyl phenylsulfoxide in the presence of an activating electrophile such as N-bromosuccinimide, N-iodosuccinimde, trifluoromethane-sulfonic anhydride and the like or metal salts such as silver trifluoromethanesulfonate, silver perchlorate, mercuric nitrate, tin chloride, and the like or a combination of an activating electrophile and a metal salt. Another alternative is reaction of the 13-epi-aglycone with a disaccharide glycal (vinyl ether) and an electrophilic activating agent such as N-iodosuccinimde or an acid such as toluenesulfonic acid, pyridinium toluenesulfonate, and the like may be used.

The process is illustrated in the following reaction scheme:

toluene, and the like with a dipyridyl disulfide such as 2,2'-dipyridyl disulfide and the like and a tri-aryl or tri-alkyl phosphine such as tributylphosphine or triphenylphosphine, and the like at temperatures ranging from 0° C. to 35° C. for one hour to 48 hours. The reaction is worked up and the glycosyl pyridylsulfide isolated and purified using standard techniques known to those skilled in the art. Reaction of the disaccharide with 2,2'-dipyridyl disulfide and tributylphosphine in dichloromethane at room temperature is preferred. The glycosylation reaction is carried out by adding a solution of the glycosyl pyridylsulfide in a non-nucleophilic solvent such as acetonitrile, ether, tetrahydrofuran (THF), chloroform, acetone, and the like to a reaction mixture consisting of a solution of the 13-epi-aglycone in the same solvent and one or more metal salts such as silver trifluoromethane-sulfonate, silver perchlorate, tin chloride, tin sulfate, mercuric chloride, copper sulfate, copper bromide, and the like with or without added

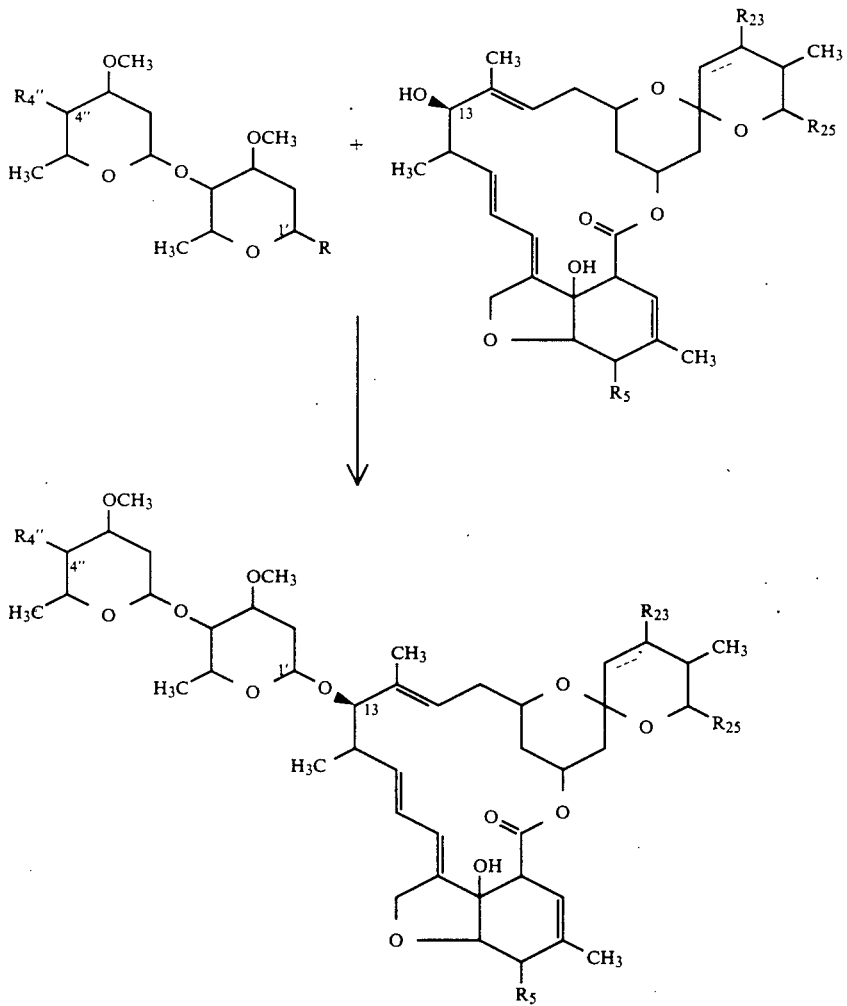

where R is halogen, pyridylthio, phenylthio, phenylsulfoxy, or phenylsulfonyl and $R_5$, $R_{23}$, $R_{25}$ and $R_{4''}$ are as defined above (except that free secondary hydroxyl groups are protected as described below).

Reaction of the aglycone with a glycosyl pyridylsulfide or a glycosyl fluoride is preferred. The glycosyl pyridylsulfide is prepared by treating a solution of the disaccharide (free anomeric OH) in a non-nucleophilic solvent such as dichloromethane, chloroform, benzene, molecular sieves at temperatures ranging from $-20°$ C. to room temperature for 15 minutes to 48 hours. The reaction is worked up and the product isolated and purified using standard techniques known to those skilled in the art. Reaction of the aglycone and the glycosyl pyridylsulfide in acetonitrile in the presence of silver trifluoromethanesulfonate is preferred. The glycosyl fluoride is prepared by treating a solution of the disaccharide (free anomeric OH) in a non-nucleophilic solvent such as dichloromethane, chloroform, and the like with a strong fluorinating agent such as diethylaminosulfur trifluoride (DAST), dimethylaminosulfur trifluoride (methyl DAST), and the like at temperatures ranging from −40° C. to room temperature for 5 minutes to one hour. The reaction is worked up and the glycosyl fluoride isolated and purified using standard techniques known to those skilled in the art. Alternatively, the glycosyl fluoride may be prepared by treating a glycosyl phenylsulfide (prepared by reaction of the disaccharide with phenyl disulfide and tributyl- or triphenyl-phosphine in an inert solvent such as benzene or dichloromethane at room temperature for 1 to 24 hours) with DAST and an electrophilic activating agent such as N-bromosuccinimide, N-iodosuccinimide, and the like in a non nucleophilic solvent such as dichloromethane, chloroform, and the like at temperatures ranging from −40° C. to room temperature for 5 minutes to one hour. The reaction is worked up and the glycosyl fluoride isolated and purified using standard techniques known to those skilled in the art. Reaction of the disaccharide with DAST in dichloromethane at room temperature is preferred. The glycosylation reaction is carried out by adding a solution of the glycosyl fluoride in a non nucleophilic solvent such as ether, tetrahydro furan (THF), chloroform, acetone, and the like to a reaction mixture consisting of a solution of the aglycone in the same solvent and one or more metal salts such as silver perchlorate, silver trifluoro-methanesulfonate, tin chloride, tin sulfate, mercuric chloride, copper sulfate and the like with or without added molecular sieves at temperatures ranging from −20° C. to room temperature for 15 minutes to 48 hours. The reaction is worked up and the product isolated and purified using standard techniques known to those skilled in the art. Reaction of the aglycone and the glycosyl fluoride in ether in the presence of silver perchlorate, tin (II) chloride, and 3A molecular sieves is preferred.

The requisite 13-epi-avermectin aglycones may be prepared by inversion of the stereochemistry at position 13 of the corresponding avermectin aglycone (for example, 13 epi avermectin $B_2$ aglycone is prepared by inversion of position 13 of avermectin $B_2$ aglycone). Preparation of the avermectin aglycones is fully described in the literature references cited above. The inversion may be accomplished by a number of procedures including nucleophilic displacement of a leaving group, such as a tosylate, mesylate, o-nitrobenzene sulfonate, and the like (prepared by reaction of the aglycone with the corresponding sulfonyl chloride using standard techniques known to those skilled in the art), at position 13 by an oxygen nucleophile such as a nitrate, a carbonate, a carboxylate, superoxide, and the like in a non nucleophilic solvent such as ether, tetrahydrofuran, dimethylformamide, benzene, and the like at temperatures ranging from room temperature to the reflux temperature of the solvent for 1 to 24 hours or, alternatively, by displacement of the aforementioned leaving group by a halide nucleophile, such as iodide, bromide, and the like in a non-nucleophilic solvent such as ether, tetrahydro-furon, dimethylformamide, benzene, and the like at temperatures ranging from room temperature to the reflux temperature of the solvent for 1 to 48 hours. The resulting halide (now with the 13-epi stereo-chemistry) may serve as a leaving group in a subsequent solvolysis reaction with water, which may be effected by treating a solution of the halide in a solvent such as tetrahydrofuran, ether, benzene and the like with water with or without added silver salts such as silver trifluoromethanesulfonate, silver tetrafluoroborate, silver nitrate, and the like at temperatures ranging from 0° C. to the reflux temperature of the solvent for 15 minutes to 24 hours. Alternatively, the 13-epi-aglycone may be prepared by reduction of a 13-ketone derivative (prepared by oxidation of the aglycone with a DMSO based reagent such as DMSO/oxalyl chloride or a chromium based reagent such as pyridinium chlorochromate using procedures well known to those skilled in the art) with an appropriate reducing agent such as sodium borohydride, diborane, lithium tri-t-butoxyaluminum hydride and the like in a solvent such as methanol, ethanol, ether and the like at temperatures ranging from 0° C. to room temperature for 15 minutes to 24 hours. Conversion of the aglycone to the 13 -epi-aglycone by reaction of the 13-tosylate with potassium iodide in dimethyl-formamide and subsequent solvolysis of the resulting 13 -epi-iodide by reaction with water in tetrahydro-furan with added silver trifluoromethanesulfonate or silver tetrafluoroborate is preferred. The reaction is worked up and the 13-epi-aglycone isolated and purified using standard procedures known to those skilled in the art.

During the preparation of the 13-epi-aglycone (by inversion of the stereochemistry of position 13) and during the attachment of the disaccharide to the 13-epi-aglycone it is necessary to protect other secondary hydroxyl groups in the molecule (note that it is not necessary to protect the tertiary hydroxyl present at position 7) with a protecting group which may be removed after the reaction is accomplished. Suitable protecting groups include tert-butyldi-methylsilyl, tert butyldiphenylsilyl, phenoxyacetyl, acetyl, and the like. The tert butyldimethylsilyl group is preferred and is introduced by treating a solution of the alcohol in dimethylformamide (DMF) with an excess of imidazole and a silylating reagent such as tert-butyldimethylsilyl-chloride, tert-butyldimethylsilyltrifluoromethanesulfonate, and the like at temperatures ranging from 25° C. to 50° C. for 4 to 48 hours. The reaction is then worked up and the product isolated and purified using standard techniques known to those skilled in the art. The Protecting group may be removed by treatment with a solution of hydrogen fluoride in a pyridine / tetrahydrofuran solvent mixture. Alternatively, the protecting group may be removed by treatment with a solution of p-toluenesulfonic acid (0.5-2%) in methanol at 0° C. to 25° C. for 0.5 to 8 hours. Deprotection with hydrogen fluoride in pyridine / tetrahydrofuran is preferred. In both cases reaction workup and product isolation and purification are by standard techniques well known to those skilled in the art.

An amino substituent may be introduced at position 4″ by reductive amination of a 4″-ketone which is in turn prepared by oxidation of the 4″-hydroxyl group present in the avermectins. The amino substituent may be introduced (and acylated if desired) either before or after coupling of the disaccharide to the aglycone (introduction before coupling is preferred). During the oxidation of the hydroxyl group at C -4″it is necessary to protect other secondary hydroxyl groups in the molecule (note that it is not necessary to protect the tertiary hydroxyl present at position 7) as described above. If the oxidation is performed on the disaccharide before coupling to the aglycone the anomeric hydroxyl may be protected by conversion of the disaccharide to the glycosyl phenylsulfide (which can be later converted to the glycosyl fluoride for glycosylation) as described above. With other secondary hydroxyl groups protected the hydroxyl group at position 4"can be oxidized by a variety of methods to afford the ketone derivatives necessary for conversion to amino and acylamino analogs. The oxidation of this hydroxyl group can be effected by using a variety of oxidation procedures, including oxidation with dimethylsulfoxide (DMSO) based systems commonly known to those skilled in the art as Swern (or Moffat) oxidations (DMSO-oxalyl-chloride, DMSO-acetic anhydride, DMSO-trifluoroacetic anhydride and the like) as well as oxidations with chromium based reagents (pyridinium chlorochromate, pyridinium dichromate, and the like), or other methods known to those skilled in the art. The DMSO based oxidations are preferred. The oxidation reagent is generated by treating a solution of DMSO in a non-nucleophilic solvent such as dichloromethane, chlorform, ether (preferred), tetrahydrofuran and the like with an electrophilic activating agent such as oxalyl chloride (preferred), dicyclohexyl carbodiimide (DCC), phosgene, and the like at temperatures ranging from $-90°$ C. to $-55°$ C. and stirring the mixture thus formed at this temperature for 10 to 90 minutes. To the oxidizing reagent thus generated is added, at the same temperature, a solution of the alcohol in the solvent used to generate the reagent. The solution is stirred at temperatures ranging form $-90°$ C. to $-55°$ C. for 10 to 90 minutes then a hindered base such as triethylamine, diisopropylethylamine, and the like is added. The temperature is raised to $0°$ C. to $30°$ C. and the mixture stirred at this temperature for 10 to 90 minutes. The reaction is then worked up and the product isolated and purified using standard techniques known to those skilled in the art.

The 4"-ketone functionality thus generated may be used to introduce amino substituents at position 4"-via a reductive amination reaction. The reductive amination affords an avermectin mixture consisting of both possible stereoisomers at position 4"(4"-alpha-amino and 4"-beta amino) which is referred to herein as 4"-amino-avermectin. The reductive amination is accomplished by treating a solution of the ketone in an alcoholic solvent such as methanol, ethanol, and the like with an ammonium salt such as ammonium acetate (preferred), ammonium formate, ammonium benzoate and the like at temperatures ranging from $-25°$ C. to $25°$ C. for 15 to 60 minutes then adding sodium cyanoborohydride to the resulting mixture and stirring at temperatures ranging from $0°$ C. to $30°$ C. for 30 to 90 minutes. The reaction is then worked up and the product isolated and purified using standard techniques known to those skilled in the art. The reaction may be modified by substituting an alkylammonium salt in the place of ammonium acetate in the above procedure to prepare avermectin derivatives substituted with an alkylamino group at the 4"position.

The amino (or alkylamino) substituted derivatives prepared as described above may be acylated to provide acylamino analogs. The acylation is accomplished by treating a solution of the 4"amino or 4"-alkylamino analog in a halogenated solvent such as dichloromethane, chloroform or the like with one molar equivalent of an acylating agent such as an alkanoyl chloride (preferred), alkanoyl bromide, alkanoic acid in combination with dicyclohexylcarbodiimide, and the like in the presence of a base such as triethylamine, pyridine and the like with or without the addition of a nucleophilic catalyst such as dimethylaminopyridine at temperatures ranging from $-10°$ C. to $35°$ C. for 15 minutes to 24 hours. The reaction is then worked up and the product isolated and purified using standard techniques known to those skilled in the art. Note that it is not necessary to protect secondary alcohols in the molecule during the acylation reaction as the amino functionality is sufficiently more reactive that acylation occurs selectively at nitrogen.

Oximes may be generated at position 5 via the 5-ketone. This ketone is prepared by oxidation of a compound with a 5-hydroxyl group using one of the oxidation methods described above. Oxidation with manganese dioxide is preferred. The oxidation is carried out by treating a solution Of the alcohol in a non-hydroxylic solvent such as benzene, dichloromethane, chloroform, tetrahydrofuran, and the like with an excess of manganese dioxide at temperatures ranging from $25°$ C. to the reflux temperature of the solvent for 4 to 48 hours. The reaction is worked up and the product isolated and purified using standard techniques known to those skilled in the art. The ketone thus generated may be used to prepare oximes or alkoximes by a number of procedures. Generally, an excess of hydroxylamine hydrochloride or the appropriate alkoyxlamine hydrochloride (methoxylamine hydrochloride for a methoxime, etc.) is added to a solution of the ketone in pyridine and the solution stirred at temperatures ranging from $0°$ C. to $50°$ C. for 3-36 hours. Alternatively the amine hydrochloride is added to a solution of the ketone in a neutral solvent such as benzene, tetrahydrofuran, dioxane, dichloromethane, ethanol, and the like following by a molar equivalent of a base such as sodium acetate, sodium hydroxide, triethylamine, and the like. The resulting mixture is stirred at temperatures ranging from $0°$ C. to $50°$ C. for 3-36 hours. In either case the reaction is worked up and the product isolated and purified using standard techniques known to those skilled in the art.

The instant compounds of this invention are unexpectedly potent antiparastic agents against endo and ecto parasites, particularly helminths and arthropods, which cause numerous parasitic diseases in humans, animals, and plants. In addition, the instant compounds are unexpectedly less toxic to mammals than are the corresponding compounds with the natural stereochemistry at position 13.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oestophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasites at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofialaia in dogs, Nematospiroides and Syphacia in rodents, biting insects, and migrating diperous larvae such as Hypoderma sp, in cattle, and Gastrophilus in horses.

The instant compounds are also useful against endo and ecto parasites which cause parasitic diseases in humans. Examples of such endoparasites which infect man include gastro-intestinal parasites of the genera, Ancylostoma, Necator, Ascaris, Strongyloides, Trichinella, Capillaria, Trichuris, Enterobius, and the like. Other endoparasites which infect man are found in the blook or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), tineola sp. (clothes moth), Attagenus sp. (carpet bettle), *Musca domestica* (housefly) and against *Solenopsis Invicta* (imported fire ant).

The compounds are furthermore useful against agricultural pests such as aphids (Acyrthiosiphon sp.), locusts, and boll weevils as well as against insect pests which attack stores grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single does of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, elemental analysis, and the like. Being amorphous the compounds are not characterized by sharp melting points but the chromatographic and analytical methods employed indicate that they are pure.

EXAMPLE 1

5-0-t-butyldimethylsilyl-22,23-dihydro-avermectin $B_1$ aglycone tert-Butyldimethylsilyl chloride (851 mg) was added to a solution of 22,23-dihydro-avermectin B1 aglycone (3.0 g, prepared as described in Chabala et al, *J. Med. Chem.* 1980, 23, 1134) and imidazole (873 mg) in 10 ml of dry dimethylformamide and the solution stirred at room temperature for 22 hours. The reaction mixture was partitioned between ether (50 ml) and water (100 ml). The aqueous layer was extracted with ether (2 ×20 ml) and the combined organic layers dried with magnesium sulfate, filtered and evaporated. The crude product was purified on a silica gel column eluted with 12.5% acetone in hexane to afford 1.97 g of a white foam which was identified by 1H NMR and mass spectrometry as 5-0-t-butyl-dimethylsilyl-22,23-dihydro-avermectin B1 aglycone. Elemental analysis: calculated for C40H64O8Si: C, 68.53; H, 9.20; Found: C, 68.40; H, 9.47.

EXAMPLE 2

5-O-t-butyldimenthylsilyil-avermectin B1-aglycone tert Butyldimethylsilyl chloride (35 mg) was added to a solution of avermectin B1 aglycone (124 mg, prepared as described in Mrozik et al, *J. Org. Chem.* 1982, 47, 489) and imidazole (36 mg) in 2.5 ml of dry dimethylformamide and the solution stirred at room temperature for 24 hours. The reaction mixture was partitioned between ether (25 ml) and water (25 ml). The aqueous layer was extracted with ether (20 ml) and the combined organic layers dried with magnesium sulfate, filtered and evaporated. The crude product was purified by preparative layer chromatography on a 2.0 mm silica gel plate eluted with 25% acetone in hexane to afford 82 mg of a white foam which was identified by 1H NMR and mass spectrometry as 5-0- t-butyldimethylsilyl-avermectin B1 aglycone.

EXAMPLE 3

5,23-bis-O-t-butyldimethylsilyl-avermectin B2-aglycone tert-Butyldimethylsilyl chloride (1.15 g) is added to a solution of avermectin B2 aglycone (2.0 g, prepared as described in prepared as described in Mrozik et al, *J. Org. Chem.* 1982, 47, 489) and imidazole (1.30 g) in 10 ml of dry dimethylformamide and the solution is stirred at room temperature for 22 hours. The reaction mixture is then partitioned between ether (50 ml) and water (100 ml). The aqueous layer is extracted with ether (2 ×20 ml) and the combined organic layers dried with magnesium sulfate, filtered and evaporated. The crude produ:t is purified on a silica gel column eluted with 12.5% acetone in hexane to afford 5,23-bis-O-t-butyldi-methylsilyl-avermectin methylsilyl avermectin B2-aglycone which is identified by 1H NMR and mass spectrometry. Elemental analysis: calculated for C46H78O9Si2 C, 66.46; H, 9.46; Found: C, 66.51; H, 9.80.

EXAMPLE 4

5-O-t-butyldimethylsilyl-13-beta-iodo-13-deoxy-22,23-dihydro-avermectin $B_1$-aglycone A solution of o-nitro-benzenesulfonyl chloride (2.40 g) in 40 ml of dry dichloromethane was added dropwise over a period of 1.5 hours to a solution of 5-O-t-butyl-dimethylsilyl-22,23 dihydro-avermectin B1 aglycone (2.30 g), dimethylamino-pyridine (1.7 g), tetrabutylammonium iodide (4.6 g) and diisopropylethylamine (2.77 ml) in 40 ml of dry dichloromethane. The resulting solution was stirred at room temperature for 16.5 hours then partitioned between dichloromethane (20 ml) and 1M aqueous NaH2PO4 (40 ml). The organic layer was washed with 1N HCl (40 ml) and water (40 ml) then dried over MgSO4, filtered, and evaporated. The orange brown tarry residue was extracted repeatedly with 30 ml portions of hot ether until analytical TLC indicated that all of the product had been extracted. The combined ether extracts were dried over MgSO4, filtered, and evaporated. The residue was purified on a silica gel column eluted with 9% acetone in hexane to afford 1.36 g of a white foam ($R_f$ 0.38) which was identified by 1H NMR and mass spectro-metry as 5-O-t butyl-dimethylsilyl-13-beta-iodo-13-deoxy-22, 23-dihydro-avermectin B1-aglycone. An additional 601 mg of impure material was obtained by concentration of fractions containing the product plus impurities.

EXAMPLE 5 5-O-t butyldimethylsilyl-13-beta-iodo-13-deoxy avermectin $B_1$ -aglycone Application of the procedure described above (Example 4) for the preparation of 5-O-t-butyl-dimethylsi-lyl-13-beta-iodo-13-deoxy-22,23-dihyro-avermectin b1-aglycone to 5-O-t-butyldimethylsilyl-13-beta-iodo-13-deoxy-avermectin b1-aglycone which is identified by 1H NMR and mass spectrometry.

EXAMPLE 6 5,23-bis-O-t-butyldimethylsilyl-13-beta-iodo-13-deoxy-avermectin B$_2$-aglycone Toluenesulfonic anhydride (3.0 g) was added to a solution of 5,23-bis-O-t butyldimethylsilyl-avermectin B$_2$-aglycone (1.5 g), dimethylamino-pyridine (1.1 g), and diisopropylethylamine (2.2 ml) in 15 ml of deutero-chloroform (note that deutero-chloroform is used as the solvent so that the reaction may be followed easily by NMR, alternatively chloroform may be used as the solvent and the reaction allowed to proceed for a predetermined time). The mixture was stirred at room temperature for 16 hours then partitioned quickly between dichloromethane (25 ml) and water (25 ml). The aqueous layer was extracted with dichloromethane (3 ×25 ml) and the combined organic layers dried over MgSO$_4$, filtered and evaporated. The resulting orange oil was dissolved in 25 ml of dry dimethyl-formamide then potassium iodide (3.3 g) was added. The mixture was stirred at 60° C. for 75 minutes then cooled to room temperature and partitioned between ether (50 ml) and water (50 ml). The aqueous layer was extracted with ether (3 ×50 ml) and the combined organic layers dried over MgSO$_4$, filtered and evaporated. The residue was purified on a silica gel column eluted with 4% acetone in hexane to afford 520 mg of a white foam (R$_f$ 0.20) which was identified by $^1$H NMR and mass spectrometry as 5,23-bis-O-t-butyldimethylsilyl-13-beta-iodo-13-deoxy-avermectin B$_2$-aglycone. Elemental analysis: calculated for C$_{46}$H$_{77}$O$_8$Si$_2$I: C, 58.70; H, 8.24; Found: C, 58.79; H, 8.52.

EXAMPLE 7 13-beta-iodo-13-deoxy-avermectin A$_1$-aglycone

Application of the procedure desribed above (Example 4) for the preparation of 5-O-t-butyldi-methylsilyl-13-beta-iodo-13-deoxy-22,23-dihydro-avermectin B$_1$-aglycone to avermectin A$_1$-aglycone affords 13-beta-iodo-13-deoxy-avermectin A$_1$aglycone which is identified by $^1$H NMR and mass spectrometry.

EXAMPLE 8 5-O-t-butyldimethylsilyl-13-epi-22,23-dihydro-avermectin B$_1$-aglycone Silver trifluoromethanesulfonate (118 mg) was added to a solution of 5-O-t-butyldimethylsilyl-13-beta-iodo-13-deoxy-22,23-dihydro-avermectin B$_1$-aglycone (371 mg) and 2,6-lutidine (0.081 ml) in 4 ml of 9:1 tetrahydrofuran:water. The mixture (white precipitate) was stirred at room temperature for 45 minutes then diluted with ether (5 ml) and filtered. Water (3 ml) was added to the filtrate and the pH adjusted to ca. 3 by addition of 2N HCl. The aqueous layer was extracted with ether (3 ml) and the combined organic layers dried over MgSO$_4$, filtered and evaporated. The residue was chromatographed on two 2 mm silica gel plates eluted four times with 33% ether in hexane to afford 144 mg of a white foam (R$_f$ 0.48) which was identified by $^1$H NMR and mass spectrometry as 5-O-t-butyldimethylsilyl 13-epi-22,23-dihydro-avermectin B$_1$-aglycone.

EXAMPLE 9 5O-t-butyldimethylsilyl-13-epi-avermectin B$_1$-aglycone

Application of the procedure described above (Example 8) for the preparation of 5-O-t-butyl-dimethylsilyl-13-epi-22,23-dihydro-avermectin B$_1$ aglycone to 5-O-t-butyldimethylsilyl 13-beta-iodo-13-deoxy-avermectin B$_1$-aglycone affords 5-O-t-butyldimethylsilyl-13-epi-avermectin B$_1$-aglycone which is identified by $^1$H NMR and mass spectrometry.

EXAMPLE 10 5,23-bis-O-t-butyldimethylsilyl-13-epi-avermectin B$_2$-aglycone

Silver trifluoromethanesulfonate (410 mg) was added to a solution of 5,23-bis-O-t-butyldimethyl-silyl-13-beta-iodo-13-deoxy-avermectin B$_2$-aglycone (520 mg) and 2,6 lutidine (0.37 ml) in 9 ml of 9:1 tetrahydrofuran:water. The mixture (yellow-white precipitate) was stirred at room temperature for 45 minutes then partitioned between ether (50 ml) and 0.1N HCl (25 ml). The layers were separated and the organic layer was washed with 25 ml of 5% aqueous NaHCO$_3$ then dried over MgSO$_4$, filtered and evaporated. The residue was chromatographed on four 1.5 mm silica gel plates eluted twice with 33% ether in hexane to afford 280 mg of a white foam (R$_f$ 0.45) which was identified by $^1$H NMR and mass spectrometry as 5,23 bis-O-t butyldimethylsilyl 13-epi-avermectin B$_2$ aglycone. Elemental analysis: calculated for C$_{46}$H$_{78}$O$_9$Si$_2$: C, 66.46; H, 9.46; Found: C, 66.25; H, 9.20.

EXAMPLE 11 13-epi-avermectin A$_1$-aglycone

Application of the procedure described above (Example 8) for the preparation of 5O-t-butyldimethylsilyl-13-epi-22,23-dihydro-avermectin B$_1$ aglycone to 13-beta-iodo-13 deoxy-avermectin A$_1$-aglycone affords 13-epi-avermectin A$_1$-aglycone which is identified by $^1$H NMR and mass spectrometry.

EXAMPLE 12 1'fluoro-4'-(4''-O-t-butyldimethysilyl-oleandrosyl-oleandorse

Diethylaminosulfur trifluoride (0.325 m1) was added to a cold ( −20° C.) solution of 686 mg of 4'-(4'-O-t-butyldimethylsilyl-oleandrosyl)-oleandrose (prepared as described in Blizzard et al J. Org. Chem. 1989, 54, 1756) in 7 ml of dry dichloromethane/ The cold bath was removed and the solution stirred at room temperature for 15 minutes then cooled to 0° C. Methanol (0.5 ml) was added and the solution was stirred at 0° C. for two minutes. Saturated aqueous NaHCO$_3$ (4 ml) was added and the layers were separated. The aqueous layer was extracted with ether (4 ×4 ml) and the combined organic layers dried over MgSO$_4$, filtered and evaporated. The residue was chromatographed on a silica gel column eluted with 25% ether in hexane to afford 473 mg of a syrup (R$_f$ 0.23) which was identified by $^1$H NMR and mass spectrometry as 1'-fluoro-4'-(4''-O-t-butyldimethylsilyl-oleandrosyl)-oleandrose.

EXAMPLE 13 140-phenylthio-4'-(4''-O-t-butyldimethylsilyl-oleandrosyl)-oleandrose Tributylphosphine (0.426 ml) was added to a solution of 4'-(4''-O-t-butyldimethylsilyl olean-drosyl)-oleandrose (600 mg) and phenyl disulfide (373 mg) in 5 ml of dry benzene. The solution was stirred at room temperature for 44 hours then the solvent was evaporated and the residue chromatographed on a silica gel column eluted with 25% ether in hexane to afford 680 mg of a syrup which was identified by $^1$H NMR and mass spectrometry as 1'-phenylthio-4'-(4"-O-t-butyldimethylsilyl-oleandrosyl)-oleandrose (mixture of isomers at C-1', avermectin numbering). The anomeric mixture can be separated by chromatogaphy on silica gel if desired.

EXAMPLE 14

1'-(2-pyridylthio)-4'-(4"-O-t-butyldimethylsilyl-oleandrosyl)-oleandrose

Tributylphosphine (1.08 ml) was added to a solution of 4'-(4"-O-t-butyldimethylsilyl-olean-drosyl)-oleandrose (1.826 g) and 2,2'-dipyridyl disulfide (956 mg) in 15 ml of dry dichloromethane. The solution was stirred at room temperature for 23 hours then the solvent was evaporated. The residual dark yellow oil was chromatographed on a silica gel column eluted with 20% ethyl acetate in hexane to afford 1.78 g of a colorless syrup ($r_f$ 0.24) which was identified by $^1$H NMR and mass spectrometry as 1'-(2-pyridylthio-4'-(4"-O-t-butyldimethyl-silyl-oleandrosyl)-oleandrose (mixture of isomers at C-1', avermectic numbering).

EXAMPLE 15

1'-phenylthio-4'-(4"-acetylamino-4"deoxy-oleandrosyl)-oleandrose

One milliliter (1ml) of a deprotection reagent solution consisting of a mixture of 25 g of hydrogen fluoride pyridine complex, 10 ml of pyridine, and 27.5 ml of tetrahydrofuran was added to a solution of 46 mg of 140-phenylthio-4"-(4"-O-t-butyldimethylsilyloleandrosyl)-oleandrose in 12 ml of dry tetrahydrofuran. The solution was stirred at room temperature for 67 hours then cooled in an ice bath as pyridine (2 ml) was added followed by ether (4 ml) and 5% aqueous NaHCO$_3$ (4 ml). The layers were separated and the aqueous layer was extracted with ether (3 ×3 ml). The combined organic layers were dried over MgSO$_4$, filtered and evaporated to a yellow oil. This crude product (1'-phenylthio-4'-oleandrosyl-oleandrose) was dissolved in 2 ml of dry dichloromethane and the resulting solution was added to a cold (−78° C.) oxidizing reagent generated by adding oxalyl chloride (0.024 ml) to a cold ( −78° C.) solution of DMSO (0.045 ml) in 2 ml of dry dichloromethane and stirring the resulting solution for 20 minutes at −78° C. The resulting mixture was stirred at −78° C. for 1 hour then triethylamine (0.125 ml) was added and the cold bath removed. The mixture was allowed to warm to room temperature and stirred at room temperature for 1 hour. The mixture was diluted with dichloromethane (3 ml) then water (5 ml) was added and the layers were separated. The aqueous layer was extracted with dichloromethane (3 ×5 ml) and the combined organic layers dried over MgSO$_4$, filtered and evaporated to a yellow oil. This crude oxidation product (1'-phenylthio-4'-(4"-oxo-4"-deoxy-oleandrosyl)-oleandrose) was dissolved in 2 ml of dry methanol than 3A molecular sieves were added followed by ammonium acetate (69 mg). The mixture was stirred at room temperature for 30 minutes then sodium cyanoborohydride (20 mg) was added in two portions (ca. 10 minutes apart). The mixture was stirred at room temperature for 2 hours then centrifuged. The supernatant was decanted and the solid residue washed with dichloromethane (2 ×3 ml). The combined supernatants were added to 3 ml of 5% aqueous NaHCO$_3$. The layers were separated and the aqueous layer extracted with dichloromethane (2 ×3 ml). The combined organic layers were dried over MgSO$_4$, filtered and evaporated to a yellow oil. The crude amine (1'-phenylthio-440-(4"-amino-4"-deoxy-oleandrosyl)-oleandrose) thus obtained was dissolved in 2 ml of dry dichloromethane then triethylamine (0.038 ml) was added. The mixture was cooled to 0° C. then acetyl chloride (0.010 ml) was added and the mixture stired at 0° C. for 1 hour. Water (2 ml) was then added followed by dichloromethane (2 ml). The layers were separated and the aqueous layer extracted with dichloromethane (2 ×3 ml). The combined organic layers were dried over MgSO$_4$, filtered and evaporated to a yellow oil. The crude product was chromatographed on a 1 mm silica gel plate eluted with 3.5% methanol in dichloromethane to afford 12 mg of a colorless syrup ($R_f$ 0.22) which was identified by $^1$H NMR and mass spectrometry as 1'-phenylthio-4'-(4"-acetylamino-4"-deoxy-oleandrosyl)-oleandrose.

EXAMPLE 16

1'-(2-pyridylthio)-4'-(4"-acetylamino-4"deoxy-oleandrosyl)-oleandrose

Tetrabutylammonium fluoride (2.3 ml of a 1M solution in tetrahydrofuran) was added to a solution of 290 ml of 1'-(2-pyridylthio)-4'-(4"-O-t-butyldimethylsilyl-oleandrosyl)-oleandrose in 6 ml of dry tetrahydrofuran. The solution was stirred at room temperature for 50 minutes then partitioned between ether (3 ml) and saturated aqueous NaCl (3 ml). The layers were separated and the aqueous layer was extracted with ether (3 ×5 ml). The combined organic layers were dried over MgSO$_4$, filtered and evaporated to an oil. This crude product (1'-pyridylylthio)-4'-oleandrosyl-oleandrose) may be purified by column chromatography on silica gel if desired. Application of the oxidation/reductive amination/acetylation procedure described above (Example 15) for the preparation of 1'-phenylthio-4'-(4"-acetylamino-4"-deoxy-oleandrosyl)-oleandrose to 1'-(2-pyridylylthio)-4'-oleandrosyl-oleandrose affords 1'-(2-pyridylylthio)-4 '-(b 4"-acetylamino-4"-deoxy-oleandrosyl)-oleandrose (separable mixture of isomers at C-4") which is identified by $^1$H NMR and mass spectrometry.

EXAMPLE 17

1'-fluoro-4'-(4"-acetylamino-4"-deoxy-oleandrosyl)-oleandrose

Diethylaminosulfur trifluoride (0.100 ml) is added to a cold ( −20° C.) solution of 200 mg of 1'-phenylthio-4'-(4"-acetylamino-oleandrosyl)-oleandrose in 4 ml of dry dichloromethane then N-bromo-succinimide (122 mg) is added. The mixture is stirred at −20° C. for 20 minutes then 3 ml of 5% aqueous NaHCO$_3$ is added. The layers are separated and the aqueous layer is extracted with dichloromethane (2 ×3 ml). The combined organic layers are dried over MgSO$_4$, filtered and evaporated. The residue is chromatographed on a silica gel column to afford 1'-fluoro-4'-(4"-acetylamino-oleandrosyl)-oleandrose (separable mixture of isomers at C-4") which is identified by $^1$H NMR and mass spectrometry.

EXAMPLE 18

4",5,23-tris-O-t-butyldimethylsilyl-13-epi-avermectin B$_2$

A solution of 560 mg of 1'-(2-pyridylthio)-4'-(4"-O-t-butyldimethylsilyl-oleandrosyl)-oleandrose in 4 ml of dry acetonitrile was added slowly dropwise (over a period of 30 minutes) to a cold (0° C.), rapidly stirring, solution of 5,23 bis-O-t-butyldimethylsilyl-13-epi-avermectin B$_2$-aglycone (500 mg) and silver trifluoromethanesulfonate (270 mg) in 6 ml of dry acetonitrile. The resulting mixture (gummy precipitate) was stirred vigorously at 0° C. for 3 hours then partitioned between ethyl acetate (15 ml) and 5% aqueous NaHCO$_3$ (10 ml). The layers were separated with the aid of a centrifuge. The aqueous layer was extracted with ethyl acetate (4 ×6 ml). The combined organic layers were dried over MgSO$_4$, filtered, and evaporated. The residue was chromographed on a silica gel column eluted with 9% acetone in hexane to afford 270 mg of a white foam which was identified by $^1$H NMR and mass spectrometry as 4'',5,23-tris-O-t-butyldimethylsilyl-13-epi-avermectin B$_2$. A by-product of the reaction was also obtained as a white foam (250 mg) and identified by $^1$H NMR and mass spectrometry as 4'',5,23-tris-O-t-butyldimethylsilyl-1',13-bis-epi-avermectin B$_2$ (1'-beta isomer).

EXAMPLE 19

4'',5,23-tris-O-t-butyldimethylsilyl-13-epi-avermectin B$_2$ (alternative procedure)

A solution of 265 mg of 1'-fluoro-4'-(4''-O-t-butyldimethylsilyl-oleandrosyl)-oleandrose in 7 ml of dry ether was added dropwise to a cold (0° C.) mixture of 5,23-bis-O-t-butyldimethylsilyl-13-epi-avermectin B$_2$-aglycone (260 mg), silver perchlorate (81 mg), tin (II) chloride (74 mg), 3A molecular sieves and 7 ml of dry ether. The resulting mixture was stirred vigorously at 0° C. for 2 hours then diluted with ether (5 ml) and centrifuged. The supernatant was decanted and the residue washed with ether (2 ×5 ml). The combined supernatants were washed with 5% aqueous NaHCO$_3$ (7 ml) and saturated NaCl (7 ml) then dried over MgSO$_4$, filtered, and evaporated. The residue was chromatographed on four 1.5 mm silica gel plates eluted twice with 9% acetone in hexane to afford 80 mg of a white foam (R$_f$ 0.27) which was identified by $^1$H NMR and mass spectrometry as 4'',5,23-tris-O-t butyldimethylsilyl-13-epi-avermectin B$_2$.

EXAMPLE 20

5-O-t-butyldimethylsilyl-4''-acetylamino-4''-deoxy-13-epi-22,23-dihydro-avermectin B$_1$ Substitution of 1'-fluoro-4'-(4''-acetyl-amino-4''-deoxy-oleandrosyl)-oleandrose for 1'-fluoro-4'-(4''-O-t-butyldimethylsilyl-oleandrosyl) -oleandrose and 5O-t-butyldimethylsilyl-13-epi-22,23-dihydro-avermectin B$_1$-aglycone for 5,23-bis-O-t-butyldimethylsilyl-13-epi-avermectin B$_2$-aglycone in the procedure of Example 19 affords 5-O-t-buytldimethylsilyl-4''-acetylamino-4''-deoxy-13-epi-22,23-dihydro-avermectin B$_1$ (separable mixture of isomers at C-4'') which is identified by $^1$H NMR and mass spectrometry.

EXAMPLE 21

5-O-t-butyldimethylsilyl-4''-acetylamino-4''-deoxy-13-epi-avermectin B$_1$

Substitution of 1'-(2-pyridylthio)-4'-(4''-acetylamino-4'''-deoxy-oleandrosyl)-oleandrose for 1'-(2-pyridyl-thio)-4'-(4'''-O-t-butyldimethylsilyl-oleandrosyl)oleandrose and 5-O-t-butyldimethylsilyl-13-epi-avermectin B$_1$-aglycone for 5,23-bis-O-t-butyldimethyl-silyl-13-epi-avermectin B$_2$-aglycone in the procedure of Example 18 affords 5-O-t-butyldimethylsilyl-4''-acetylamino-4''-deoxy-13-epi-avermectin B$_1$ which is identified by $^1$H NMR and mass spectrometry.

EXAMPLE 22

4'',5-bis-O-t-butyldimethylsilyl-13-epi-avermectin B$_1$

Substitution of 5-O-t-butyldimethylsilyl-13-epi-avermectin B$_1$-aglycone for 5,23-bis-O-t-butyldimethylsilyl-13-epi-avermectin B$_2$-aglycone in the procedure of Example 18 affords 4'',5-bis-O-t-butyldimethylsilyl-13-epi-avermectin B$_1$ which is identified by $^1$H NMR and mass spectrometry.

EXAMPLE 23

4''-O-t-butyldimethylsilyl-13-epi-avermectin A$_1$

Substitution of 13-epi-avermectin A$_1$-aglycone for 5,23-bis-O-t-butyldimethylsilyl-13-epi-avermectin B$_2$-aglycone in the procedure of Example 18 affords 4''-O-t-butyldimethylsilyl-13-epi-avermectin A$_1$ which is identified by $^1$H NMR and mass spectrometry.

EXAMPLE 24

13-epi-avermectin B$_2$

A deprotection reagent solution was prepared by cautiously adding 25 g of hydrogen fluoride pyridine complex to a cold (0° C.) mixture of pyridine (12.5 ml) of the resulting reagent solution was added to a cold (0° C.) solution of 389 mg of 4'',5,23-tris-O-t-butyldimethylsilyl-13-epi-avermectin B$_2$ in 7 ml of dry tetrahydrofuran. The resulting solution was stirred at room temperature for 112 hours then cooled in an ice bath as pyridine (6 ml) was added followed by ethyl acetate (10 ml) and 5% aqueous NaHCO$_3$ (12 ml). The layers were separated with the aid of a centrifuge and the aqueous layer was extracted with ethyl acetate (3 ×6 ml). The combined organic layers were dried over MgSO$_4$ and K$_2$CO$_3$, filtered and evaporated to a light yellow oil (287 mg). The crude product was combined with an additional 260 mg of crude product obtained from an identical experiment. The consolidated crude product was chromatographed on a silica gel column eluted with 25% acetone in hexane to afford 370 mg of a white foam (R$_f$ 0.09) which was identified by $^1$H NMR and mass spectrometry as 13-epi avermectin B$_2$. Elemental analysis: calculated for C$_{48}$H$_{74}$O$_{15}$: C, 64.70; H, 8.47; found: C, 64.40; H, 8.47.

EXAMPLE 25

4''-acetylamino-4''-deoxy-13-epi-22,23-dihydro-avermectin B$_1$

Substitution of 5O-t-butyldimethylsilyl-4''-acetylamino-4''-deoxy-13-epi-22,23-dihydro-avermectin B$_1$ for 4'',4,23-tris-O-t-butyldimethylsilyl -13-epi-avermectin B$_2$ in the deprotection procedure of Example 24 affords 4''-acetylamino-4''-deoxy 13-epi-22,23-dihydro-avermectin B$_1$ (separable mixture of isomers at C-4'') which is identified by $^1$H NMR and mass spectrometry.

EXAMPLE 26

4''-acetylamino-4''-deoxy-13-epi-deoxy-avermectin B$_1$

Substitution of 5-O-t-butyldimethylsilyl-4''-acetylamino-4''-deoxy-13-epi-avermectin B$_1$ for 4'',5,23-tris-O-t-butyldimethylsilyl-13-epi-avermectin B$_2$ in the deprotection procedure of Example 24 affords 4''-acetylamino-4''-deoxy-13-epi-avermectin B$_1$ (separable mixture of isomers at C-4") which is identified by $^1$H NMR and mass spectrometry.

EXAMPLE 27

13-epi-avermectin $B_1$

Substitution of 4",5-bis-O-t-Butyldimethylsilyl-pb 13-epi-avermectin $B_1$ for 4",5,23-tris-O-t-butyldimethylsilyl-13-epi-avermectin $B_2$ in the deprotection procedure of Example 24 affords 13-epi-avermectin $B_1$ which is identified by $^1$H NMR and mass spectrometry.

EXAMPLE 28

13-epi-avermectin $A_1$

Substitution of 4"-O-t-butyldimethylsilyl-13-epi-avermectin $A_1$ for 4",5,23-tris-O-t-butyldimethylsilyl-13-epi-avermectin $B_2$ in the deprotection procedure of Example 24 affords 13-epi-avermectin $A_1$ which is identified by $^1$H NMR and mass spectrometry.

EXAMPLE 29

5-O-t-butyldimethylsilyl-13-epi-avermectin $B_1$ tert-Butyldimethylsilyl chloride (22 mg) is added to a solution of 13-epi-avermectin $B_1$ (100 mg) and imidazole (24 mg) in 1.5 ml of dry dimethylformamide and the solution is stirred at room temperature for 24 hours. The reaction mixture is partitioned between ether (15 ml) and water (15 ml). the aqueous layer is extracted with ether (20 ml) and the combined organic layers are dried with magnesium sulfate, filtered and evaporated. The crude product is chromatographed on a 1 mm silica gel plate eluted with 25% acetone in hexane to afford 5-O-t-butyldimethylsilyl-13-epi-avermectin $B_1$ which is identified by $^1$H NMR and mass spectrometry.

EXAMPLE 30

5-O-t-butyldimethylsilyl-4"-amino-4"-deoxy-13-epi-avermectin $B_1$

Oxalyl chloride (0.022 ml) is added to a cold (−78° C.) solution of DMSO (0.042 ml) in 2 ml of dry dichloromethane and the resulting solution is stirred for 20 minutes at −78° C. A solution of 5-O-t-butyldimethylsilyl-13-epi-avermectin $B_1$ (80 mg) in 2 ml of dry dichloromethane is then added. The resulting mixture is stirred at −78° C. for 1 hour then triethylamine (0.115 ml) is added and the cold bath is removed. The mixture is allowed to warm to room temperature and is stirred at room temperature for 1 hour. The mixture is diluted with dichloromethane (3 ml) then water (5 ml) is added and the layers are separated. The aqueous layer is extracted with dichloromethane (3 ×5 ml) and the combined organic layers are dried over MgSO$_4$, filtered and evaporated. This crude oxidation product (5-O-t-butyldimethylsilyl-4"-oxo-13-epi-avermectin $B_1$) is dissolved in 2 ml of dry methanol then 3A molecular sieves are added followed by ammonium acetate (62 mg). The mixture is stirred at room temperature for 30 minutes then sodium cyanoborohydride (18 mg) is added in two portions (ca. 10 minutes apart). The mixture is stirred at room temperature for 2 hours then centrifuged. The supernatant is decanted and the solid residue is washed with dichloromethane (2 ×3 ml). The combined supernatants are added to 3 ml of 5% aqueous NaHCO$_3$. The layers are separated and the aqueous layer is extracted with dichloromethane (2 ×3 ml). The combined organic layers are dried over MgSO$_4$, filtered and evaporated. The residue is chromatographed on a silica gel column to afford 5-O-t-butyldimethylsilyl-4"-amino-4"-deoxy-13-epi-avermectin $B_1$ )separable mixture of isomers at C-4") which is identified by $^1$H NMR and mass spectrometry.

EXAMPLE 31

4"-amino-4"-deoxy-13-epi-avermectin $B_1$

Substitution of 5-O-t-butyldimethylsilyl-4"-amino-4"-deoxy-13-epi-avermectin $B_1$ for 4",5,23-tris-O-t-butyldimethylsilyl-13-epi-avermectin $B_2$ in the deprotection procedure of Example 24 affords 4"-amino-4"-deoxy-13-epi-avermectin $B_1$ (separable mixture of isomers at C-4") which is identified by $^1$H NMR and mass spectrometry.

EXAMPLE 32

5-O-t-butyldimethylsilyl-4"-methylamino-4"-deoxy-13-epi-avermectin $B_1$

Substitution of methylamine hydrochloride for ammonium acetate in the reductive amination procedure of Example 30 affords 5-O-t-butyldimethylsilyl-4"-methylamino-4"-deoxy-13-epi-avermectin $B_1$ (separable mixture of isomers at C-4") which is identified by $^1$H NMR and mass spectrometry.

EXAMPLE 33

"-methylamino-4"-deoxy-13-epi-avermectin $B_1$

Substitution of 5-O-t-butyldimethylsilyl-4"-methylamino-4"-deoxy-13-epi-avermectin $B_1$ for 4",5,23-tris-O-t-butyldimethylsilyl-13-epi-avermectin $B_2$ in the deprotection procedure of Example 24 affords 4"-methylamino-4"-deoxy-13 -epi-avermectin $B_1$ (separable mixture of isomers at C-4") which is identified by $^1$H NMR and mass spectrometry.

EXAMPLE 34

5-oxo-13-epi-avermectin $B_2$

Manganese dioxide (65 mg) is added to a solution of 100 mg of 13-epi-avermectin $B_2$ in 5 ml of dry benzene. The resulting mixture is stirred at 35° C. until complete by analytical thin layer chromatography. The mixture is partitioned between water (5 ml) and ether (5 ml) and the aqueous layer extracted with ether (3 ×5 ml). The combined organic layers are dried over MgSO$_4$, filtered and evaporated. The crude product is chromatographed on a silica gel plate to afford 5-oxo-13-epi-avermectin $B_2$ which is identified by $^1$H NMR and mass spectrometry.

EXAMPLE 35

13-epi-avermectin Bphd 2-5-oxime

Hydroxylamine hydrochloride (50 mg) is added to a solution of 5-oxo-13-avermectin $B_2$ (75 mg) in 3 ml of dry pyridine. The solution is stirred at room temperature until complete by analytical thin layer chromatography. The mixture is partitioned between water (7 ml) and ether (7 ml) and the aqueous layer extracted with ether (3 ×5 ml). The combined organic layers are dried over MgSO$_4$, filtered and evaporated. The crude product is chromatographed on a silica gel plate to afford 13-epi-avermectin $B_2$-5-oxime which is identified by $^1$H NMR and mass spectrometry.

What is claimed is:
1. A compound having the formula:

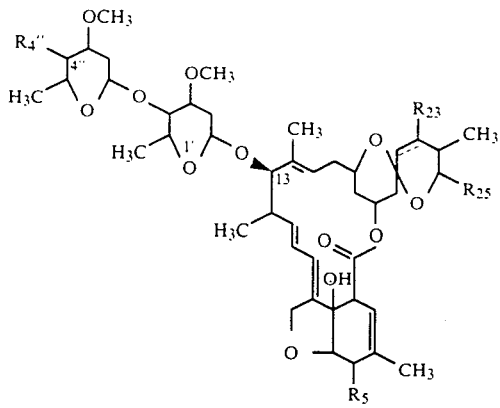

wherein:
$R_{4''}$ = OH, NH$_2$, NH-loweralkyl, NH-loweralkyanol;
$R_5$ = OH, oxime, OCH$_3$;
$R_{23}$ = H, OH; (provided $R_{23}$ is not OH if the broken line indicates a double bond);
$R_{25}$ = loweralkyl; and
the broken line indicates a single or double bond at the 22,23 position, provided that the broken line is not a single bond if $R_{4''}$=OH and $R_{23}$=H.

2. The compound of claim 1 wherein $R_{4''}$=OH, NH$_2$, NH-loweralkyl, NH-loweralkyanoyl; $R_5$ =OH;
$R_{23}$ = H, OH;
$R_{25}$ = isopropyl or secbutyl; and
the broken line indicates a single or double bond.

3. The compound of claim 2 wherein
$R_{4''}$=OH, NH-methyl, NH-acetyl;
$R_5$ = OH;
$R_{23}$ = H, OH; and
the broken line indicates a single or double bond.

4. The compound of claim 3 wherein
$R_{4''}$=OH, NH-acetyl;
$R_{23}$ = H, OH; and
the broken line indicates a single or double bond.

5. The compound of claim 1 which is 13-epi-avermectin B$_1$.

6. The compound of claim 1 which is 13-epi-avermectin B$_2$.

7. The compound of claim 1 which is 13-epi-avermectin A$_1$.

8. The compound of claim 1 which is 4''-epi-amino-4''-deoxy-13-epi-avermectin B$_2$.

9. The compound of claim 1 which is 4''-epi-methylamino-4''-deoxy-13-epi-avermectin B$_1$.

10. The compound of claim 1 which is 4''-epi-methylamino-4''-deoxy-13-epi-avermectin B$_2$.

11. The compound of claim 1 which is 4''-epi-acetylamino-4''-deoxy-13-epi-avermectin B$_1$.

12. The compound of claim 1 which is 4''-epi-acetylamino-4''-deoxy-13-epi-22,23-dihydro-avermectin B$_1$.

13. The compound of claim 1 which is 4''-acetylamino-4''-deoxy-13-avermectin B$_2$.

14. The compound of claim 1 which is 4''-acetylamino-4''-deoxy-13-epi-avermectin B$_2$.

15. The compound of claim 1 which is 13-epi-avermectin B$_2$-5-oxime.

16. The compound of claim 1 which is 13-epi-avermectin B$_1$-5-oxime.

17. A method for the treatment and/or prevention of parasitic infections in animals which comprises treating such animals with an effective amount of a compound of claim 1.

18. A method for the treatment of pests of plants which comprises treating said plants or the soil in which they grow with an effective amount of a compound of claim 1.

19. A composition useful for the treatment and/or prevention of parasitic infections of animals which is comprised of an inert carrier and a compound of claim 1.

20. A composition useful for the treatment of pests of plants which is comprised of an inert carrier and a compound of claim 1.

* * * * *

UNITED STATES PATENT AND TRADEMARK OFFICE
CERTIFICATE OF CORRECTION

PATENT NO. : 5,055,454

DATED : October 8, 1991

INVENTOR(S) : Timothy A. Blizzard, et al

It is certified that error appears in the above-identified patent and that said Letters Patent is hereby corrected as shown below:

The title page should be deleted to appear as per attached title page.

The sheets consisting of cols. 3-24, should be deleted to be replaced with cols. 1-24 as per attached sheets.

Signed and Sealed this

Twenty-second Day of December, 1992

Attest:

DOUGLAS B. COMER

Attesting Officer

Acting Commissioner of Patents and Trademarks

United States Patent [19]

Blizzard et al.

[11] Patent Number: 5,055,454
[45] Date of Patent: Oct. 8, 1991

[54] 13-EPI-AVERMECTIN DERIVATIVES USEFUL AS ANTIPARASITIC AGENTS

[75] Inventors: Timothy A. Blizzard, Rahway; Helmut Mrozik, Matawan, both of N.J.

[73] Assignee: Merck & Co., Inc., Rahway, N.J.

[21] Appl. No.: 429,920

[22] Filed: Oct. 30, 1989

[51] Int. Cl.$^5$ .................... A61K 31/70; C07D 315/00
[52] U.S. Cl. ...................................... 514/30; 514/450; 514/336; 549/264; 536/7.1; 546/268
[58] Field of Search ............... 536/7.1; 549/264; 514/450, 30

[56] References Cited

U.S. PATENT DOCUMENTS

| | | | |
|---|---|---|---|
| 3,950,360 | 4/1976 | Aoki et al. | 549/264 |
| 4,171,314 | 10/1979 | Chabala et al. | 549/264 |
| 4,173,571 | 11/1979 | Chabala et al. | 549/264 |
| 4,310,519 | 1/1982 | Albers-Schonberg et al. | 536/7.1 |
| 4,587,247 | 5/1986 | Linn et al. | 549/264 |

FOREIGN PATENT DOCUMENTS

| | | |
|---|---|---|
| 170006 | 2/1986 | European Pat. Off. |
| 235085 | 9/1987 | European Pat. Off. |
| 2166436 | 5/1986 | United Kingdom |

OTHER PUBLICATIONS

Albers–Schonberg et al. (II), *J. Am Chem Soc.* 103, pp. 4216–4221 (1981).
Chabala et al. (III), *J. Med Chem.*, 23, pp. 1134–1136 (1980).
Mrozik et al., *J. Org. Chem.*, 47, pp. 489–492 (1982).
Carter et al., *J. Antibiotics*, 41, pp. 519–529 (1988).
Blizzard et al., *J. Org. Chem.*, 54, p. 1756 (1989).

*Primary Examiner*—C. Warren Ivy
*Assistant Examiner*—Amelia A. Owens
*Attorney, Agent, or Firm*—David L. Rose; Joseph F. DiPrima

[57] ABSTRACT

There are disclosed avermectin derivatives in which position 13 of the avermectins has been inverted from the normal (alpha) stereochemistry to the epimeric 13-beta stereochemistry. The synthetic 13-epi analogs are derived from the corresponding aglycones which in turn are prepared by chemical modification of naturally occurring avermectins. The compounds are active antiparasitic agents and compositions for that use are disclosed.

20 Claims, No Drawings

13-EPI-AVERMECTIN DERIVATIVES USEFUL AS ANTIPARASITIC AGENTS

BACKGROUND OF THE INVENTION

The avermectins (previously referred to as C-076 compounds) are a series of compounds produced by fermentation of avermectin producing strains of *Streptomyces avermitilis* and derivatives thereof. The morphological characteristics of the culture are completely described in U.S. Pat. No. 4,310,519. The production, isolation, and structure determination of the avermectins are fully described in Albers-Schonberg et al *J. Am. Chem. Soc.* 1981, 103, 4216–4221 and references cited therein. The conversion of natural avermectin $B_1$ to 22,23-dihydro-avermectin $B_1$, the potent broad spectrum anthelminthic agent known as ivermectin, has also been described in the literature (Chabala et al *J. Med. Chem.* 1980, 23, 1134–1136). The naturally occurring avermectins and the instant derivatives thereof have a very high degree of anthelminthic and anti-parasitic activity.

The naturally occurring avermectins are a series of macrocyclic lactones which are substituted at position 13 with a disaccharide consisting of two oleandrose residues. The preparation and properties of synthetic avermectin aglycones in which the disaccharide moiety has been removed leaving a free hydroxyl group at position 13 have been described by Mrozik et al *J. Org. Chem.* 1982, 47, 489–492 and by Chabala et al *J. Med Chem.* 1980, 23, 1134–1136. The natural compounds have the following general structure:

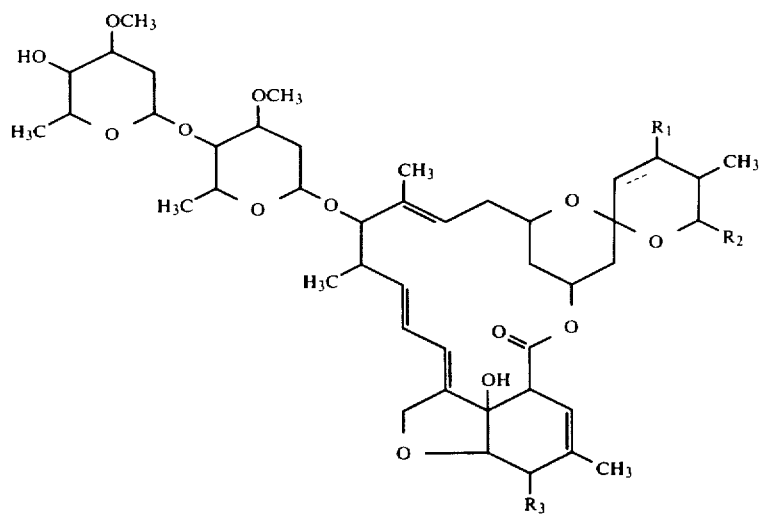

wherein the broken line indicates a single or double bond and;

$R_1$ is hydroxy and is present only when said broken line indicates a single bond;

$R_2$ is iso-propyl or sec-butyl; and $R_3$ is methoxy or hydroxy.

There are eight major natural avermectin compounds, designated $A_{1a}$, $A_{1b}$, $A_{2a}$, $A_{2b}$, $B_{1a}$, $B_{1b}$, $B_{2a}$ and $B_{2b}$. These designations are based on the structure of the individual compounds as shown in the following table (referring to the foregoing structural formula).

| Compound | broken line | $R_1$ | $R_2$ | $R_3$ |
|---|---|---|---|---|
| $A_{1a}$ | double bond | — | sec-butyl | —$OCH_3$ |
| $A_{1b}$ | double bond | — | iso-propyl | —$OCH_3$ |
| $A_{2a}$ | single bond | —OH | sec-butyl | —$OCH_3$ |
| $A_{2b}$ | single bond | —OH | iso-propyl | —$OCH_3$ |
| $B_{1a}$ | double bond | — | sec-butyl | —OH |
| $B_{1b}$ | double bond | — | iso-propyl | —OH |
| $B_{2a}$ | single bond | —OH | sec-butyl | —OH |
| $B_{2b}$ | single bond | —OH | iso-propyl | —OH |

The avermectins are generally isolated as mixtures of the a and b components (typically $\geq 80\%$ a and $\leq 20\%$ b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components is indicated by dropping the a or b from the designation of the compound. A mixture of avermectin $B_{1a}$ and avermectin $B_{1b}$ is thus referred to as avermectin $B_1$.

A related family of natural products is known as the milbemycins. The milbemycins have the same basic structure as the avermectins but have no substitution at position 13 and have a methyl or ethyl group at position 25 ($R_2$=methyl or ethyl rather than isopropyl or sec-butyl as in the avermectins). The milbemycins and the fermentation conditions used to prepare them are described in U.S. Pat. No. 3,950,360. Closely related 13-deoxy-avermectin aglycones are prepared by chemical modification of the natural avermectins and have been described in U.S. Pat. Nos. 4,171,134 and 4,173,571.

Recently a number of related compounds have been described in European Patent Application EPO 170,006 and U.K. application 2,166,436 (see also Carter et al, *J. Antibiotics* 1988, 41, 519–529). These compounds are essentially 13-deoxy-avermectin aglycones in which the $R_2$ side chain contains a double bond and, in some cases, includes additional carbon atoms. Finally, a recent European Patent Application, EPO 235085, describes the conversion of various milbemycins to the 13-beta-glycosyloxy analogs.

SUMMARY OF THE INVENTION

This invention is concerned with certain avermectin derivatives in which the stereochemistry at position 13 is the opposite of the natural stereochemistry and the use of these derivatives as antiparasitic agents. Thus it is an object of this invention to describe these avermectin derivatives. A further object of this invention is to describe processes for the preparation of these compounds. A still further object is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objects will become apparent from a reading of the following description.

DESCRIPTION OF THE INVENTION

The compounds of the instant invention are best realized in the following structure:

wherein the broken line indicates a single or double bond at the 22,23 position;

$R_{4''}$ = OH, $NH_2$, NH-loweralkyl, NH-loweralkanoyl;
$R_5$ = OH, oxime, $OCH_3$;
$R_{23}$ = H, OH, provided $R_{23}$ is not OH if the broken line indicates a double bond; and
$R_{25}$ = loweralkyl.

In the instant invention "loweralkyl" is intended to include those alkyl groups of from 1 to 7 carbon atoms in either a straight or branched chain. Examples of such loweralkyl groups are methyl, ethyl, propyl, isopropyl, butyl, sec-butyl, pentyl, hexyl, heptyl, and the like.

The term "loweralkanoyl" is intended to include those alkanoyl groups of from 1 to 7 carbon atoms in either a straight or branched chain. Examples of such loweralkanoyl groups are formyl, acetyl, propionyl, isopropionyl, butyryl, sec-butyryl, pentanoyl, hexanoyl, heptanoyl, and the like.

Preferred compounds of this invention are realized when:

$R_{4''}$ = OH, $NH_2$, NH-loweralkyl, NH-loweralkanoyl;
$R_5$ = OH, oxime, $OCH_3$;
$R_{23}$ = H, OH;
$R_{25}$ = loweralkyl; and
the broken line indicates a single or double bond (provided that the broken line does not indicate a single bond if $R_{4''}$ = OH and $R_{23}$ = H).

More preferred compounds of this invention are realized when:

$R_{4''}$ = OH, $NH_2$, NH-loweralkanoyl;
$R_5$ = OH;
$R_{23}$ = H, OH;
$R_{25}$ = isopropyl or sec-butyl;
and the broken line indicates a single or double bond.

Still more preferred compounds of this invention are realized when:

$R_{4''}$ = OH, NH-loweralkanoyl;
$R_{23}$ = H, OH; and
the broken line indicates a single or double bond.

The most preferred compounds of this invention are realized when:

$R_{4''}$ = OH, NH-acetyl;
$R_{23}$ = H, OH,
and the broken line indicates a single or double bond.

Examples of the preferred compounds of this invention are as follows:

13-epi- avermectin $B_1$
13-epi-avermectin $B_2$
13-epi-avermectin $A_1$
13-epi-avermectin $A_2$
4''-deoxy-4''-amino-13-epi-avermectin $B_1$
4''-epi-amino-4''deoxy-13-epi-avermectin $B_1$
4''-amino-4''deoxy-13-epi-22,23-dihydro-avermectin $B_1$
4''-epi-amino-4''-deoxy-13-epi-22,23-dihydro-avermectin $B_1$
4''-amino-4''-deoxy-13-epi-avermectin $B_2$
4''-epi-amino-4''deoxy-13-epi-avermectin $B_2$
4''-methylamino-4''deoxy-13-epi-avermectin $B_1$
4''-epi-methylamino-4''deoxy-13-epi-avermectin $B_1$
4''-methylamino-4''deoxy-13-epi-22,23-dihydro-avermectin $B_1$
4''-epi-methylamino-4''deoxy-13-epi-22,23-dihydro-avermectin $B_1$
4''-methylamino-4''deoxy-13-epi-avermectin $B_2$
4''-epi-methylamino-4''deoxy-13-epi-avermectin $B_2$
4''-acetylamino-4''deoxy-13-epi-avermectin $B_1$
4''-epi-acetylamino-4''deoxy-13-epi-avermectin $B_1$
4''-acetylamino-4''deoxy-13-epi-22,23-dihydro-avermectin $B_1$
4''-epi-acetylamino-4''deoxy-13-epi-22,23-dihydro-avermectin $B_1$
4''-acetylamino-4''deoxy-13-epi-avermectin $B_2$
4''-acetylamino-4''deoxy-13-epi-avermectin $B_2$
13-epi-avermectin $B_1$-5-oxime
13-epi-avermectin $B_2$-5-oxime

PREPARATION OF STARTING MATERIALS

The starting materials for this invention are disclosed in Albers-Schonberg et al. *J. Am. Chem. Soc.* 1981, 103, 4216–4221 and references cited therein (naturally occurring avermectins), Chabala et al *J. Med. Chem.* 1980, 23, 1134–1136 (22,23-dihydro-avermectin $B_1$ (ivermectin), and 22,23-dihydro-avermectin $B_1$-aglycone), Mrozik et al *J. Org. Chem.* 1982, 47, 489–492 (avermectin aglycones), Mrozik et al *J. Med. Chem.* 1989, 32, 375–381 (13-epi-avermectin aglycones), Linn et al U.S. Pat. No. 4,587,247, and Blizzard et al *J. Org. Chem.* 1989, 54, 1756 (avermectin disaccharide).

The novel compounds of this invention are prepared by the following procedures:

The instant compounds are prepared by attaching a disaccharide unit to a 13-epi-avermectin aglycone. Attachment of the disaccharide may be effected by a variety of glycosylation procedures such as reaction of the aglycone with a glycosyl fluoride or other halide in the presence of one or more salts of various metals such as silver, tin, mercury, copper and the like. An alternative procedure involves reaction of the aglycone with a glycosyl phenylsulfide or a glycosyl pyridylsulfide or a glycosyl phenylsulfoxide in the presence of an activating electrophile such as N-bromosuccinimide, N-iodosuccinimide, trifluoromethane-sulfonic anhydride and the like or metal salts such as silver trifluoromethanesulfonate, silver perchlorate, mercuric nitrate, tin chloride, and the like or a combination of an activating electrophile and a metal salt. Another alternative is reaction of the 13-epi-aglycone with a disaccharide glycal (vinyl ether) and an electrophilic activating agent such as N-iodosuccinimide or an acid such as toluenesulfonic acid, pyridinium toluenesulfonate, and the like may be used.

The process is illustrated in the following reaction scheme:

toluene, and the like with a dipyridyl disulfide such as 2,2'-dipyridyl disulfide and the like and a tri-aryl or tri-alkyl phosphine such as tributylphosphine or triphenylphosphine, and the like at temperatures ranging from 0° C. to 35° C. for one hour to 48 hours. The reaction is worked up and the glycosyl pyridylsulfide isolated and purified using standard techniques known to those skilled in the art. Reaction of the disaccharide with 2,2'-dipyridyl disulfide and tributylphosphine in dichloromethane at room temperature is preferred. The glycosylation reaction is carried out by adding a solution of the glycosyl pyridylsulfide in a non-nucleophilic solvent such as acetonitrile, ether, tetrahydrofuran (THF), chloroform, acetone, and the like to a reaction mixture consisting of a solution of the 13-epi-aglycone in the same solvent and one or more metal salts such as silver trifluoromethane-sulfonate, silver perchlorate, tin chloride, tin sulfate, mercuric chloride, copper sulfate, copper bromide, and the like with or without added

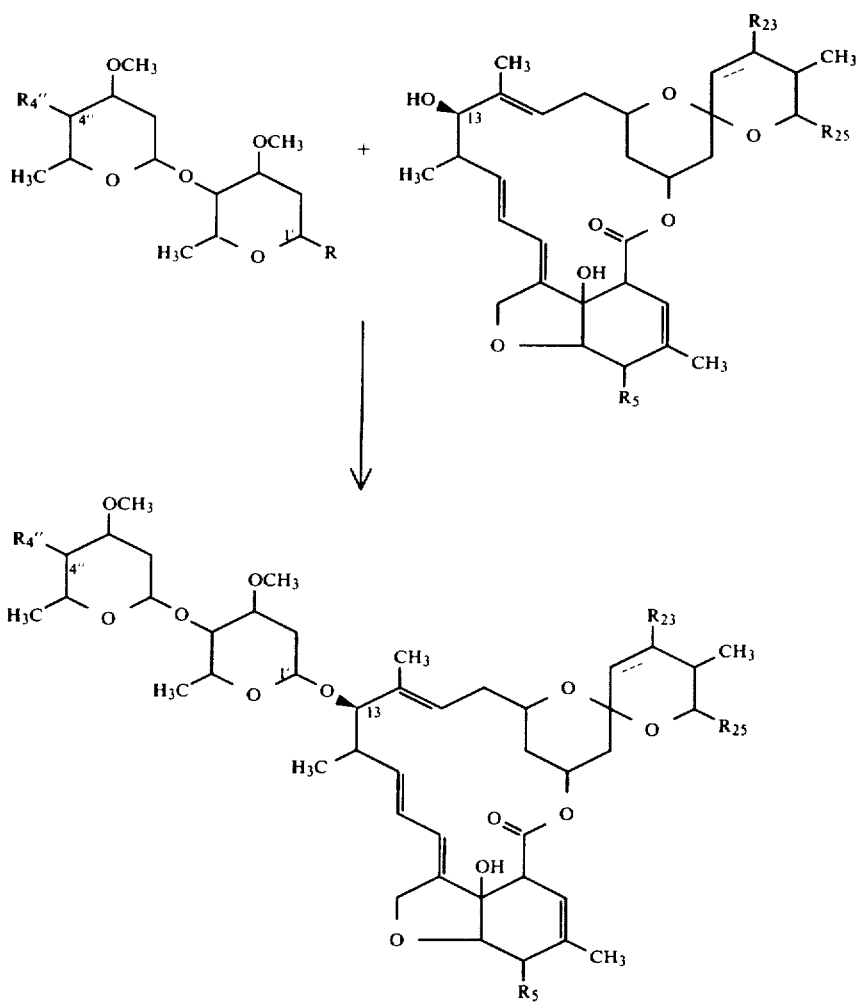

where R is halogen, pyridylthio, phenylthio, phenylsulfoxy, or phenylsulfonyl and $R_5$, $R_{23}$, $R_{25}$ and $R_{4''}$ are as defined above (except that free secondary hydroxyl groups are protected as described below).

Reaction of the aglycone with a glycosyl pyridylsulfide or a glycosyl fluoride is preferred. The glycosyl pyridylsulfide is prepared by treating a solution of the disaccharide (free anomeric OH) in a non-nucleophilic solvent such as dichloromethane, chloroform, benzene, molecular sieves at temperatures ranging from $-20°$ C. to room temperature for 15 minutes to 48 hours. The reaction is worked up and the product isolated and purified using standard techniques known to those skilled in the art. Reaction of the aglycone and the glycosyl pyridylsulfide in acetonitrile in the presence of silver trifluoromethanesulfonate is preferred. The glycosyl fluoride is prepared by treating a solution of the disaccharide (free anomeric OH) in a non-nucleophilic solvent such as dichloromethane, chloroform, and the like with a strong fluorinating agent such as diethylaminosulfur trifluoride (DAST), dimethylaminosulfur trifluoride (methyl DAST), and the like at temperatures ranging from −40° C. to room temperature for 5 minutes to one hour. The reaction is worked up and the glycosyl fluoride isolated and purified using standard techniques known to those skilled in the art. Alternatively, the glycosyl fluoride may be prepared by treating a glycosyl phenylsulfide (prepared by reaction of the disaccharide with phenyl disulfide and tributyl- or triphenyl-phosphine in an inert solvent such as benzene or dichloromethane at room temperature for 1 to 24 hours) with DAST and an electrophilic activating agent such as N-bromosuccinimide, N-iodosuccinimide, and the like in a non nucleophilic solvent such as dichloromethane, chloroform, and the like at temperatures ranging from −40° C. to room temperature for 5 minutes to one hour. The reaction is worked up and the glycosyl fluoride isolated and purified using standard techniques known to those skilled in the art. Reaction of the disaccharide with DAST in dichloromethane at room temperature is preferred. The glycosylation reaction is carried out by adding a solution of the glycosyl fluoride in a non nucleophilic solvent such as ether, tetrahydrofuran (THF), chloroform, acetone, and the like to a reaction mixture consisting of a solution of the aglycone in the same solvent and one or more metal salts such as silver perchlorate, silver trifluoro-methanesulfonate, tin chloride, tin sulfate, mercuric chloride. copper sulfate and the like with or without added molecular sieves at temperatures ranging from −20° C. to room temperature for 15 minutes to 48 hours. The reaction is worked up and the product isolated and purified using standard techniques known to those skilled in the art. Reaction of the aglycone and the glycosyl fluoride in ether in the presence of silver perchlorate, tin (II) chloride, and 3A molecular sieves is preferred.

The requisite 13-epi-avermectin aglycones may be prepared by inversion of the stereochemistry at position 13 of the corresponding avermectin aglycone (for example, 13-epi-avermectin $B_2$ aglycone is prepared by inversion of position 13 of avermectin $B_2$ aglycone). Preparation of the avermectin aglycones is fully described in the literature references cited above. The inversion may be accomplished by a number of procedures including nucleophilic displacement of a leaving group, such as a tosylate, mesylate, o-nitrobenzene sulfonate, and the like (prepared by reaction of the aglycone with the corresponding sulfonyl chloride using standard techniques known to those skilled in the art), at position 13 by an oxygen nucleophile such as a nitrate, a carbonate, a carboxylate, superoxide, and the like in a non-nucleophilic solvent such as ether, tetrahydrofuran, dimethylformamide, benzene, and the like at temperatures ranging from room temperature to the reflux temperature of the solvent for 1 to 24 hours or, alternatively, by displacement of the aforementioned leaving group by a halide nucleophile, such as iodide, bromide, and the like in a non-nucleophilic solvent such as ether, tetrahydrofuron, dimethylformamide, benzene, and the like at temperatures ranging from room temperature to the reflux temperature of the solvent for 1 to 48 hours. The resulting halide (now with the 13-epi stereochemistry) may serve as a leaving group in a subsequent solvolysis reaction with water, which may be effected by treating a solution of the halide in a solvent such as tetrahydrofuran, ether, benzene and the like with water with or without added silver salts such as silver trifluoromethanesulfonate, silver tetrafluoroborate, silver nitrate, and the like at temperatures ranging from 0° C. to the reflux temperature of the solvent for 15 minutes to 24 hours. Alternatively, the 13-epi-aglycone may be prepared by reduction of a 13-ketone derivative (prepared by oxidation of the aglycone with a DMSO based reagent such as DMSO/oxalyl chloride or a chromium based reagent such as pyridinium chlorochromate using procedures well known to those skilled in the art) with an appropriate reducing agent such as sodium borohydride, diborane, lithium tri-t-butoxyaluminum hydride and the like in a solvent such as methanol, ethanol, ether and the like at temperatures ranging from 0° C. to room temperature for 15 minutes to 24 hours. Conversion of the aglycone to the 13-epi-aglycone by reaction of the 13-tosylate with potassium iodide in dimethylformamide and subsequent solvolysis of the resulting 13-epi-iodide by reaction with water in tetrahydrofuran with added silver trifluoromethanesulfonate or silver tetrafluoroborate is preferred. The reaction is worked up and the 13-epi-aglycone isolated and purified using standard procedures known to those skilled in the art.

During the preparation of the 13-epi-aglycone (by inversion of the stereochemistry of position 13) and during the attachment of the disaccharide to the 13-epi-aglycone it is necessary to protect other secondary hydroxyl groups in the molecule (note that it is not necessary to protect the tertiary hydroxyl present at position 7) with a protecting group which may be removed after the reaction is accomplished. Suitable protecting groups include tert-butyldimethylsilyl, tert-butyldiphenylsilyl, phenoxyacetyl, acetyl, and the like. The tert-butyldimethylsilyl group is preferred and is introduced by treating a solution of the alcohol in dimethylformamide (DMF) with an excess of imidazole and a silylating reagent such as tert-butyldimethylsilylchloride, tert-butyldimethylsilyltrifluoromethanesulfonate, and the like at temperatures ranging from 25° C. to 50° C. for 4 to 48 hours. The reaction is then worked up and the product isolated and purified using standard techniques known to those skilled in the art. The protecting group may be removed by treatment with a solution of hydrogen fluoride in a pyridine/tetrahydrofuran solvent mixture. Alternatively, the protecting group may be removed by treatment with a solution of p-toluenesulfonic acid (0.5–2%) in methanol at 0° C. to 25° C. for 0.5 to 8 hours. Deprotection with hydrogen fluoride in pyridine/tetrahydrofuran is preferred. In both cases reaction workup and product isolation and purification are by standard techniques well known to those skilled in the art.

An amino substituent may be introduced at position 4″ by reductive amination of a 4″-ketone which is in turn prepared by oxidation of the 4″-hydroxyl group present in the avermectins. The amino substituent may be introduced (and acylated if desired) either before or after coupling of the disaccharide to the aglycone (introduction before coupling is preferred). During the oxidation of the hydroxyl group at C-4″ it is necessary to protect other secondary hydroxyl groups in the molecule (note that it is not necessary to protect the tertiary hydroxyl present at position 7) as described above. If the oxidation is performed on the disaccharide before coupling to the aglycone the anomeric hydroxyl may be protected by conversion of the disaccharide to the glycosyl phenylsulfide (which can be later converted to the glycosyl fluoride for glycosylation) as described above. With other secondary hydroxyl groups protected the hydroxyl group at position 4" can be oxidized by a variety of methods to afford the ketone derivatives necessary for conversion to amino and acylamino analogs. The oxidation of this hydroxyl group can be effected by using a variety of oxidation procedures, including oxidation with dimethylsulfoxide (DMSO) based systems commonly known to those skilled in the art as Swern (or Moffat) oxidations (DMSO-oxalylchloride, DMSO-acetic anhydride, DMSO-trifluoroacetic anhydride and the like) as well as oxidations with chromium based reagents (pyridinium chlorochromate, pyridinium dichromate, and the like), or other methods known to those skilled in the art. The DMSO based oxidations are preferred. The oxidation reagent is generated by treating a solution of DMSO in a non-nucleophilic solvent such as dichloromethane, chlorform, ether (preferred), tetrahydrofuran and the like with an electrophilic activating agent such as oxalyl chloride (preferred), dicyclohexyl carbodiimide (DCC), phosgene, and the like at temperatures ranging from −90° C. to −55° C. and stirring the mixture thus formed at this temperature for 10 to 90 minutes. To the oxidizing reagent thus generated is added, at the same temperature, a solution of the alcohol in the solvent used to generate the reagent. The solution is stirred at temperatures ranging form −90° C. to −55° C. for 10 to 90 minutes then a hindered base such as triethylamine, diisopropylethylamine, and the like is added. The temperature is raised to 0° C. to 30° C. and the mixture stirred at this temperature for 10 to 90 minutes. The reaction is then worked up and the product isolated and purified using standard techniques known to those skilled in the art.

The 4"-ketone functionality thus generated may be used to introduce amino substituents at position 4" via a reductive amination reaction. The reductive amination affords an avermectin mixture consisting of both possible stereoisomers at position 4" (4"-alpha-amino and 4"-beta amino) which is referred to herein as 4"-aminoavermectin. The reductive amination is accomplished by treating a solution of the ketone in an alcoholic solvent such as methanol, ethanol, and the like with an ammonium salt such as ammonium acetate (preferred), ammonium formate, ammonium benzoate and the like at temperatures ranging from −25° C. to 25° C. for 15 to 60 minutes then adding sodium cyanoborohydride to the resulting mixture and stirring at temperatures ranging from 0° C. to 30° C. for 30 to 90 minutes. The reaction is then worked up and the product isolated and purified using standard techniques known to those skilled in the art. The reaction may be modified by substituting an alkylammonium salt in the place of ammonium acetate in the above procedure to prepare avermectin derivatives substituted with an alkylamino group at the 4" position.

The amino (or alkylamino) substituted derivatives prepared as described above may be acylated to provide acylamino analogs. The acylation is accomplished by treating a solution of the 4"-amino or 4"-alkylamino analog in a halogenated solvent such as dichloromethane, chloroform or the like with one molar equivalent of an acylating agent such as an alkanoyl chloride (preferred), alkanoyl bromide, alkanoic acid in combination with dicyclohexylcarbodiimide, and the like in the presence of a base such as triethylamine, pyridine and the like with or without the addition of a nucleophilic catalyst such as dimethylaminopyridine at temperatures ranging from −10° C. to 35° C. for 15 minutes to 24 hours. The reaction is then worked up and the product isolated and purified using standard techniques known to those skilled in the art. Note that it is not necessary to protect secondary alcohols in the molecule during the acylation reaction as the amino functionality is sufficiently more reactive that acylation occurs selectively at nitrogen.

Oximes may be generated at position 5 via the 5-ketone. This ketone is prepared by oxidation of a compound with a 5-hydroxyl group using one of the oxidation methods described above. Oxidation with manganese dioxide is preferred. The oxidation is carried out by treating a solution of the alcohol in a non-hydroxylic solvent such as benzene, dichloromethane, chloroform, tetrahydrofuran, and the like with an excess of manganese dioxide at temperatures ranging from 25° C. to the reflux temperature of the solvent for 4 to 48 hours. The reaction is worked up and the product isolated and purified using standard techniques known to those skilled in the art. The ketone thus generated may be used to prepare oximes or alkoximes by a number of procedures. Generally, an excess of hydroxylamine hydrochloride or the appropriate alkoyxlamine hydrochloride (methoxylamine hydrochloride for a methoxime, etc.) is added to a solution of the ketone in pyridine and the solution stirred at temperatures ranging from 0° C. to 50° C. for 3–36 hours. Alternatively the amine hydrochloride is added to a solution of the ketone in a neutral solvent such as benzene, tetrahydrofuran, dioxane, dichloromethane, ethanol, and the like followed by a molar equivalent of a base such as sodium acetate, sodium hydroxide, triethylamine, and the like. The resulting mixture is stirred at temperatures ranging from 0° C. to 50° C. for 3–36 hours. In either case the reaction is worked up and the product isolated and purified using standard techniques known to those skilled in the art.

The instant compounds of this invention are unexpectedly potent antiparastic agents against endo and ecto parasites, particularly helminths and arthropods, which cause numerous parasitic diseases in humans, animals, and plants. In addition, the instant compounds are unexpectedly less toxic to mammals than are the corresponding compounds with the natural stereochemistry at position 13.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oestophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasites at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro-intestinal parasites of the genera, Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), *Musca domestica* (housefly) and against *Solenopsis invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compound of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, elemental analysis, and the like. Being amorphous the compounds are not characterized by sharp melting points but the chromatographic and analytical methods employed indicate that they are pure.

EXAMPLE 1

5-O-t-butyldimethylsilyl-22,23-dihydro-avermectin $B_1$ aglycone tert-Butyldimethylsilyl chloride (851 mg) was added to a solution of 22,23-dihydro-avermectin $B_1$ aglycone (3.0 g, prepared as described in Chabala et al, *J. Med. Chem.* 1980, 23, 1134) and imidazole (873 mg) in 10 ml of dry dimethylformamide and the solution stirred at room temperature for 22 hours. The reaction mixture was partitioned between ether (50 ml) and water (100 ml). The aqueous layer was extracted with ether (2×20 ml) and the combined organic layers dried with magnesium sulfate, filtered and evaporated. The crude product was purified on a silica gel column eluted with 12.5% acetone in hexane to afford 1.97 g of a white foam which was identified by $^1$H NMR and mass spectrometry as 5-O-t-butyldimethylsilyl-22,23-dihydro-avermectin $B_1$ aglycone. Elemental analysis: calculated for $C_{40}H_{64}O_8Si$: C, 68.53; H, 9.20; Found: C, 68.40; H, 9.47.

EXAMPLE 2

5-O-t-butyldimethylsilyl-avermectin $B_1$-aglycone tert-Butyldimethylsilyl chloride (35 mg) was added to a solution of avermectin $B_1$ aglycone (124 mg, prepared as described in Mrozik et al, *J. Org. Chem.* 1982, 47, 489) and imidazole (36 mg) in 2.5 ml of dry dimethylformamide and the solution stirred at room temperature for 24 hours. The reaction mixture was partitioned between ether (25 ml) and water (25 ml). The aqueous layer was extracted with ether (20 ml) and the combined organic layers dried with magnesium sulfate, filtered and evaporated. The crude product was purified by preparative layer chromatography on a 2.0 mm silica gel plate eluted with 25% acetone in hexane to afford 82 mg of a white foam which was identified by $^1$H NMR and mass spectrometry as 5-O-t-butyldimethylsilyl-avermectin $B_1$ aglycone.

EXAMPLE 3

5,23-bis-O-t-butyldimethylsilyl-avermectin $B_2$-aglycone tert-Butyldimethylsilyl chloride (1.15 g) is added to a solution of avermectin $B_2$ aglycone (2.0 g), prepared as described in prepared as described in Mrozik et al, *J. Org. Chem.* 1982, 47, 489) and imidazole (1.30 g) in 10 ml of dry dimethylformamide and the solution is stirred at room temperature for 22 hours. The reaction mixture is then partitioned between ether (50 ml) and water (100 ml). The aqueous layer is extracted with ether (2×20 ml) and the combined organic layers dried with magnesium sulfate, filtered and evaporated. The crude product is purified on a silica gel column eluted with 12.5% acetone in hexane to afford 5,23-bis-O-t-butyldimethylsilyl-avermectin $B_2$-aglycone which is identified by $^1$H NMR and mass spectrometry. Elemental analysis: calculated for $C_{46}H_{78}O_9Si_2$: C, 66.46; H, 9.46; Found: C, 66.51; H, 9.80.

EXAMPLE 4

5-O-t-butyldimethylsilyl-13-beta-iodo-13-deoxy-22,23-dihydro-avermectin $B_1$-aglycone A solution of o-nitro-benzenesulfonyl chloride (2.40 g) in 40 ml of dry dichloromethane was added dropwise over a period of 1.5 hours to a solution of 5-O-t-butyldimethylsilyl-22,23dihydro-avermectin $B_1$ aglycone (2.30 g), dimethylaminopyridine (1.7 g), tetrabutylammonium iodide (4.6 g) and diisopropylethylamine (2.77 ml) in 40 ml of dry dichloromethane. The resulting solution was stirred at room temperature for 16.5 hours then partitioned between dichloromethane (20 ml) and 1M aqueous $NaH_2PO_4$ (40 ml). The organic layer was washed with 1N HCl (40 ml) and water (40 ml) then dried over $MgSO_4$, filtered, and evaporated. The orange-brown tarry residue was extracted repeatedly with 30 ml portions of hot ether until analytical TLC indicated that all of the product had been extracted. The combined ether extracts were dried over $MgSO_4$, filtered, and evaporated. The residue was purified on a silica gel column eluted with 9% acetone in hexane to afford 1.36 g of a white foam ($R_f$ 0.38) which was identified by $^1$H NMR and mass spectrometry as 5-O-t-butyldimethylsilyl-13-beta-iodo-13-deoxy-22,23-dihydro-avermectin $B_1$-aglycone. An additional 601 mg of impure material was obtained by concentration of fractions containing the product plus impurities.

EXAMPLE 5

5-O-t butyldimethylsilyl-13-beta-iodo-13-deoxy avermectin $B_1$-aglycone

Application of the procedure described above (Example 4) for the preparation of 5-O-t-butyldimethylsilyl-13-beta-iodo-13-deoxy-22,23-dihyro-avermectin $B_1$-aglycone to 5-O-t-butyldimethylsilyl-avermectin $B_1$aglycone affords 5-O-t-butyldimethylsilyl-13-beta-iodo-13-deoxy-avermectin $B_1$-aglycone which is identified by $^1$H NMR and mass spectrometry.

EXAMPLE 6

5,23-bis-O-t-butyldimethylsilyl-13-beta-iodo-13-deoxy-avermectin B$_2$-aglycone Toluenesulfonic anhydride (3.0 g) was added to a solution of 5,23-bis-O-t-butyldimethylsilyl-avermectin B$_2$-aglycone (1.5 g), dimethylaminopyridine (1.1 g), and diisopropylethylamine (2.2 ml) in 15 ml of deuterochloroform (note that deuterochloroform is used as the solvent so that the reaction may be followed easily by NMR, alternatively chloroform may be used as the solvent and the reaction allowed to proceed for a predetermined time). The mixture was stirred at room temperature for 16 hours then partitioned quickly between dichloromethane (25 ml) and water (25 ml). The aqueous layer was extracted with dichloromethane (3×25 ml) and the combined organic layers dried over MgSO$_4$, filtered and evaporated. The resulting orange oil was dissolved in 25 ml of dry dimethylformamide then potassium iodide (3.3 g) was added. The mixture was stirred at 60° C. for 75 minutes then cooled to room temperature and partitioned between ether (50 ml) and water (50 ml). The aqueous layer was extracted with ether (3×50 ml) and the combined organic layers dried over MgSO$_4$, filtered and evaporated. The residue was purified on a silica gel column eluted with 4% acetone in hexane to afford 520 mg of a white foam (R$_f$ 0.20) which was identified by $^1$H NMR and mass spectrometry as 5,23-bis-O-t-butyldimethylsilyl-13-beta-iodo-13-deoxy-avermectin B$_2$-aglycone. Elemental analysis: calculated for C$_{46}$H$_{77}$O$_8$Si$_2$I: C, 58.70; H, 8.24; Found: C, 58.79; H, 8.52.

EXAMPLE 7

13-beta-iodo-13-deoxy-avermectin A$_1$-aglycone

Application of the procedure described above (Example 4) for the preparation of 5-O-t-butyldimethylsilyl-13-beta-iodo-13-deoxy-22,23-dihydro-avermectin B$_1$-aglycone to avermectin A$_1$-aglycone affords 13-beta-iodo-13-deoxy-avermectin A$_1$-aglycone which is identified by $^1$H NMR and mass spectrometry.

EXAMPLE 8

5-O-t-butyldimethylsilyl-13-epi-22,23-dihydro-avermectin B$_1$-aglycone

Silver trifluoromethanesulfonate (118 mg) was added to a solution of 5-O-t-butyldimethylsilyl-13-beta-iodo-13-deoxy-22,23-dihydro-avermectin B$_1$-aglycone (371 mg) and 2,6-lutidine (0.081 ml) in 4 ml of 9:1 tetrahydrofuran:water. The mixture (white precipitate) was stirred at room temperature for 45 minutes then diluted with ether (5 ml) and filtered. Water (3 ml) was added to the filtrate and the pH adjusted to ca. 3 by addition of 2N HCl. The aqueous layer was extracted with ether (3 ml) and the combined organic layers dried over MgSO$_4$, filtered and evaporated. The residue was chromatographed on two 2 mm silica gel plates eluted four times with 33% ether in hexane to afford 144 mg of a white foam (R$_f$ 0.48) which was identified by $^1$H NMR and mass spectrometry as 5-O-t-butyldimethylsilyl-13-epi-22,23-dihydro-avermectin B$_1$-aglycone.

EXAMPLE 9

5-O-t-butyldimethylsilyl-13-epi-avermectin B$_1$-aglycone

Application of the procedure described above (Example 8) for the preparation of 5-O-t-butyldimethylsilyl-13-epi-22,23-dihydro-avermectin B$_1$-aglycone to 5-O-t-butyldimethylsilyl-13-beta-iodo-13-deoxy-avermectin B$_1$-aglycone affords 5-O-t-butyldimethylsilyl-13-epi-avermectin B$_1$-aglycone which is identified by $^1$H NMR and mass spectrometry.

EXAMPLE 10

5,23-bis-O-t-butyldimethylsilyl-13-epi-avermectin B$_2$-aglycone

Silver trifluoromethanesulfonate (410 mg) was added to a solution of 5,23-bis-O-t-butyldimethylsilyl-13-beta-iodo-13-deoxy-avermectin B$_2$-aglycone (520 mg) and 2,6-lutidine (0.37 ml) in 9 ml of 9:1 tetrahydrofuran:water. The mixture (yellow-white precipitate) was stirred at room temperature for 45 minutes then partitioned between ether (50 ml) and 0.1N HCl (25 ml). The layers were separated and the organic layer was washed with 25 ml of 5% aqueous NaHCO$_3$ then dried over MgSO$_4$, filtered and evaporated. The residue was chromatographed on four 1.5 mm silica gel plates eluted twice with 33% ether in hexane to afford 280 mg of a white foam (R$_f$ 0.45) which was identified by $^1$H NMR and mass spectrometry as 5,23-bis-O-t-butyldimethylsilyl-13-epi-avermectin B$_2$ aglycone. Elemental analysis: calculated for C$_{46}$H$_{78}$O$_9$Si$_2$: C, 66.46; H, 9.46; Found: C, 66.25; H, 9.20.

EXAMPLE 11

13-epi-avermectin A$_1$-aglycone

Application of the procedure described above (Example 8) for the preparation of 5-O-t-butyldimethylsilyl-13-epi-22,23-dihydro-avermectin B$_1$-aglycone to 13-beta-iodo-13-deoxy-avermectin A$_1$-aglycone affords 13-epi-avermectin A$_1$-aglycone which is identified by $^1$H NMR and mass spectrometry.

EXAMPLE 12

1'-fluoro-4'-(4''-O-t-butyldimethylsilyl-oleandrosyl)-oleandrose

Diethylaminosulfur trifluoride (0.325 ml) was added to a cold (−20° C.) solution of 686 mg of 4'-(4''-O-t-butyldimethylsilyl-oleandrosyl)-oleandrose (prepared as described in Blizzard et al *J. Org. Chem.* 1989, 54, 1756) in 7 ml of dry dichloromethane. The cold bath was removed and the solution stirred at room temperature for 15 minutes then cooled to 0° C. Methanol (0.5 ml) was added and the solution was stirred at 0° C. for two minutes. Saturated aqueous NaHCO$_3$ (4 ml) was added and the layers were separated. The aqueous layer was extracted with ether (4×4 ml) and the combined organic layers dried over MgSO$_4$, filtered and evaporated. The residue was chromatographed on a silica gel column eluted with 25% ether in hexane to afford 473 mg of a syrup (R$_f$ 0.23) which was identified by $^1$H NMR and mass spectrometry as 1'-fluoro-4'-(4''-O-t-butyldimethylsilyl-oleandrosyl)-oleandrose.

EXAMPLE 13

1'-phenylthio-4'-(4''-O-t-butyldimethylsilyl-oleandrosyl)-oleandrose

Tributylphosphine (0.426 ml) was added to a solution of 4'-(4''-O-t-butyldimethylsilyl-oleandrosyl)-oleandrose (600 mg) and phenyl disulfide (373 mg) in 5 ml of dry benzene. The solution was stirred at room temperature for 44 hours then the solvent was evaporated and the residue chromatographed on a silica gel column eluted with 25% ether in hexane to afford 680 mg of a syrup which was identified by $^1$H NMR and mass spectrometry as 1'-phenylthio-4'-(4"-O-t-butyldimethylsilyl-oleandrosyl)-oleandrose (mixture of isomers at C-1', avermectin numbering). The anomeric mixture can be separated by chromatogaphy on silica gel if desired.

EXAMPLE 14

1'-(2-pyridylthio)-4'-(4"-O-t-butyldimethylsilyl-oleandrosyl)-oleandrose

Tributylphosphine (1.08 ml) was added to a solution of 4'-(4"-O-t-butyldimethylsilyl-oleandrosyl)-oleandrose (1.826 g) and 2,2'-dipyridyl disulfide (956 mg) in 15 ml of dry dichloromethane. The solution was stirred at room temperature for 23 hours then the solvent was evaporated. The residual dark yellow oil was chromatographed on a silica gel column eluted with 20% ethyl acetate in hexane to afford 1.78 g of a colorless syrup ($R_f$ 0.24) which was identified by $^1$H NMR and mass spectrometry as 1'-(2-pyridylthio-4'-(4"-O-t-butyldimethylsilyl-oleandrosyl)-oleandrose (mixture of isomers at C-1', avermectin numbering).

EXAMPLE 15

1'-phenylthio-4'-(4"-acetylamino-4"deoxy-oleandrosyl)-oleandrose

One milliliter (1 ml) of a deprotection reagent solution consisting of a mixture of 25 g of hydrogen fluoride pyridine complex, 10 ml of pyridine, and 27.5 ml of tetrahydrofuran was added to a solution of 46 mg of 1'-phenylthio-4'-(4"-O-t-butyldimethylsilyloleandrosyl)-oleandrose in 2 ml of dry tetrahydrofuran. The solution was stirred at room temperature for 67 hours then cooled in an ice bath as pyridine (2 ml) was added followed by ether (4 ml) and 5% aqueous NaHCO$_3$ (4 ml). The layers were separated and the aqueous layer was extracted with ether (3×3 ml). The combined organic layers were dried over MgSO$_4$, filtered and evaporated to a yellow oil. This crude product (1'-phenylthio-4'-oleandrosyl-oleandrose) was dissolved in 2 ml of dry dichloromethane and the resulting solution was added to a cold (−78° C.) oxidizing reagent generated by adding oxalyl chloride (0.024 ml) to a cold (−78° C.) solution of DMSO (0.045 ml) in 2 ml of dry dichloromethane and stirring the resulting solution for 20 minutes at −78° C. The resulting mixture was stirred at −78° C. for 1 hour then triethylamine (0.125 ml) was added and the cold bath removed. The mixture was allowed to warm to room temperature and stirred at room temperature for 1 hour. The mixture was diluted with dichloromethane (3 ml) then water (5 ml) was added and the layers were separated. The aqueous layer was extracted with dichloromethane (3×5 ml) and the combined organic layers dried over MgSO$_4$, filtered and evaporated to a yellow oil. This crude oxidation product (1'-phenylthio-4'-(4"-oxo-4"-deoxy-oleandrosyl)-oleandrose) was dissolved in 2 ml of dry methanol then 3A molecular sieves were added followed by ammonium acetate (69 mg). The mixture was stirred at room temperature for 30 minutes then sodium cyanoborohydride (20 mg) was added in two portions (ca. 10 minutes apart). The mixture was stirred at room temperature for 2 hours then centrifuged. The supernatant was decanted and the solid residue washed with dichloromethane (2×3 ml). The combined supernatants were added to 3 ml of 5% aqueous NaHCO$_3$. The layers were separated and the aqueous layer extracted with dichloromethane (2×3 ml). The combined organic layers were dried over MgSO$_4$, filtered and evaporated to a yellow oil. The crude amine (1'-phenylthio-4'-(4"-amino-4"-deoxy-oleandrosyl)-oleandrose) thus obtained was dissolved in 2 ml of dry dichloromethane then triethylamine (0.038 ml) was added. The mixture was cooled to 0° C. then acetyl chloride (0.010 ml) was added and the mixture stired at 0° C. for 1 hour. Water (2 ml) was then added followed by dichloromethane (2 ml). The layers were separated and the aqueous layer extracted with dichloromethane (2×3 ml). The combined organic layers were dried over MgSO$_4$, filtered and evaporated to a yellow oil. The crude product was chromatographed on a 1 mm silica gel plate eluted with 3.5% methanol in dichloromethane to afford 12 mg of a colorless syrup ($R_f$ 0.22) which was identified by $^1$H NMR and mass spectrometry as 1'-phenylthio-4'-(4"-acetylamino-4"-deoxy-oleandrosyl)-oleandrose.

EXAMPLE 16

1'-(2-pyridylthio)-4'-(4"-acetylamino-4"deoxy-oleandrosyl)-oleandrose

Tetrabutylammonium fluoride (2.3 ml of a 1M solution in tetrahydrofuran) was added to a solution of 290 ml of 1'-(2-pyridylthio)-4'-(4"-O-t-butyldimethylsilyl-oleandrosyl)-oleandrose in 6 ml of dry tetrahydrofuran. The solution was stirred at room temperature for 50 minutes then partitioned between ether (3 ml) and saturated aqueous NaCl (3 ml). The layers were separated and the aqueous layer was extracted with ether (3×5 ml). The combined organic layers were dried over MgSO$_4$, filtered and evaporated to an oil. This crude product (1'-pyridylylthio)-4'-oleandrosyl-oleandrose) may be purified by column chromatography on silica gel if desired. Application of the oxidation/reductive amination/acetylation procedure described above (Example 15) for the preparation of 1'-phenylthio-4'-(4"-acetylamino-4"-deoxy-oleandrosyl)-oleandrose to 1'-(2-pyridylylthio)-4'-oleandrosyl-oleandrose affords 1'-(2-pyridylylthio)-4'-(4"-acetylamino-4"-deoxy-oleandrosyl)-oleandrose (separable mixture of isomers at C-4") which is identified by $^1$H NMR and mass spectrometry.

EXAMPLE 17

1'-fluoro-4'-(4"-acetylamino-4"-deoxy-oleandrosyl)-oleandrose

Diethylaminosulfur trifluoride (0.100 ml) is added to a cold (−20° C.) solution of 200 mg of 1'-phenylthio-4'-(4"-acetylamino-oleandrosyl)-oleandrose in 4 ml of dry dichloromethane then N-bromo-succinimide (122 mg) is added. The mixture is stirred at −20° C. for 20 minutes then 3 ml of 5% aqueous NaHCO$_3$ is added. The layers are separated and the aqueous layer is extracted with dichloromethane (2×3 ml). The combined organic layers are dried over MgSO$_4$, filtered and evaporated. The residue is chromatographed on a silica gel column to afford 1'-fluoro-4'-(4"-acetylamino-oleandrosyl)-oleandrose (separable mixture of isomers at C-4") which is identified by $^1$H NMR and mass spectrometry.

EXAMPLE 18

4″,5,23-tris-O-t-butyldimethylsilyl-13-epi-avermectin B$_2$

A solution of 560 mg of 1′-(2-pyridylthio)-4′-(4″-O-t-butyldimethylsilyl-oleandrosyl)-oleandrose in 4 ml of dry acetonitrile was added slowly dropwise (over a period of 30 minutes) to a cold (0° C.), rapidly stirring, solution of 5,23-bis-O-t-butyldimethylsilyl-13-epi-avermectin B$_2$-aglycone (500 mg) and silver trifluoromethanesulfonate (270 mg) in 6 ml of dry acetonitrile. The resulting mixture (gummy precipitate) was stirred vigorously at 0° C. for 3 hours then partitioned between ethyl acetate (15 ml) and 5% aqueous NaHCO$_3$ (10 ml). The layers were separated with the aid of a centrifuge. The aqueous layer was extracted with ethyl acetate (4×6 ml). The combined organic layers were dried over MgSO$_4$, filtered, and evaporated. The residue was chromographed on a silica gel column eluted with 9% acetone in hexane to afford 270 mg of a white foam which was identified by $^1$H NMR and mass spectrometry as 4″,5,23-tris-O-t-butyldimethylsilyl-13-epi-avermectin B$_2$. A by-product of the reaction was also obtained as a white foam (250 mg) and identified by $^1$H NMR and mass spectrometry as 4″,5,23-tris-O-t-butyldimethylsilyl-1′,13-bis-epi-avermectin B$_2$ (1′-beta isomer).

EXAMPLE 19

4″,5,23-tris-O-t-butyldimethylsilyl-13-epi-avermectin B$_2$ (alternative procedure)

A solution of 265 mg of 1′-fluoro-4′-(4″-O-t-butyldimethylsilyl-oleandrosyl)-oleandrose in 7 ml of dry ether was added dropwise to a cold (0° C.) mixture of 5,23-bis-O-t-butyldimethylsilyl-13-epi-avermectin B$_2$-aglycone (260 mg), silver perchlorate (81 mg), tin (II) chloride (74 mg), 3A molecular sieves and 7 ml of dry ether. The resulting mixture was stirred vigorously at 0° C. for 2 hours then diluted with ether (5 ml) and centrifuged. The supernatant was decanted and the residue washed with ether (2×5 ml). The combined supernatants were washed with 5% aqueous NaHCO$_3$ (7 ml) and saturated NaCl (7 ml) then dried over MgSO$_4$, filtered, and evaporated. The residue was chromatographed on four 1.5 mm silica gel plates eluted twice with 9% acetone in hexane to afford 80 mg of a white foam (R$_f$ 0.27) which was identified by $^1$H NMR and mass spectrometry as 4″,5,23-tris-O-t-butyldimethylsilyl-13-epi-avermectin B$_2$.

EXAMPLE 20

5-O-t-butyldimethylsilyl-4″-acetylamino-4″-deoxy-13-epi-22,23-dihydro-avermectin B$_1$ Substitution of 1′-fluoro-4′-(4″-acetyl-amino-4″-deoxy-oleandrosyl)-oleandrose for 1′-fluoro-4′-(4″-O-t-butyldimethylsilyl-oleandrosyl)-oleandrose and 5-O-t-butyldimethylsilyl-13-epi-22,23-dihydro-avermectin B$_1$-aglycone for 5,23-bis-O-t-butyldimethylsilyl-13-epi-avermectin B$_2$-aglycone in the procedure of Example 19 affords 5-O-t-butyldimethylsilyl-4″-acetylamino-4″-deoxy-13-epi-22,23-dihydro-avermectin B$_1$ (separable mixture of isomers at C-4″) which is identified by $^1$H NMR and mass spectrometry.

EXAMPLE 21

5-O-t-butyldimethylsilyl-4″-acetylamino-4″-deoxy-13-epi-avermectin B$_1$

Substitution of 1′-(2-pyridylthio)-4′-(4″-acetylamino-4″-deoxy-oleandrosyl)-oleandrose for 1′-(2-pyridyl-thio)-4′-(4″-O-t-butyldimethylsilyl-oleandrosyl)oleandrose and 5-O-t-butyldimethylsilyl-13-epi-avermectin B$_1$-aglycone for 5,23-bis-O-t-butyldimethyl-silyl-13-epi-avermectin B$_2$-aglycone in the procedure of Example 18 affords 5-O-t-butyldimethylsilyl-4″-acetylamino-4″-deoxy-13-epi-avermectin B$_1$ which is identified by $^1$H NMR and mass spectrometry.

EXAMPLE 22

4″,5-bis-O-t-butyldimethylsilyl-13-epi-avermectin B$_1$

Substitution of 5-O-t-butyldimethylsilyl-13-epi-avermectin B$_1$-aglycone for 5,23-bis-O-t-butyldimethylsilyl-13-epi-avermectin B$_2$-aglycone in the procedure of Example 18 affords 4″,5-bis-O-t-butyldimethylsilyl-13-epi-avermectin B$_1$ which is identified by $^1$H NMR and mass spectrometry.

EXAMPLE 23

4″-O-t-butyldimethylsilyl-13-epi-avermectin A$_1$

Substitution of 13-epi-avermectin A$_1$-aglycone for 5,23-bis-O-t-butyldimethylsilyl-13-epi-avermectin B$_2$-aglycone in the procedure of Example 18 affords 4″-O-t-butyldimethylsilyl-13-epi-avermectin A$_1$ which is identified by $^1$H NMR and mass spectrometry.

EXAMPLE 24

13-epi-avermectin B$_2$

A deprotection reagent solution was prepared by cautiously adding 25 g of hydrogen fluoride pyridine complex to a cold (0° C.) mixture of pyridine (12.5 ml) and tetrahydrofuran (27.5 ml. A portion (2.1 ml) of the resulting reagent solution was added to a cold (0° C.) solution of 389 mg of 4″,5,23-tris-O-t-butyldimethylsilyl-13-epi-avermectin B$_2$ in 7 ml of dry tetrahydrofuran. The resulting solution was stirred at room temperature for 112 hours then cooled in an ice bath as pyridine (6 ml) was added followed by ethyl acetate (10 ml) and 5% aqueous NaHCO$_3$ (12 ml). The layers were separated with the aid of a centrifuge and the aqueous layer was extracted with ethyl acetate (3×6 ml). The combined organic layers were dried over MgSO$_4$ and K$_2$CO$_3$, filtered and evaporated to a light yellow oil (287 mg). The crude product was combined with an additional 260 mg of crude product obtained from an identical experiment. The consolidated crude product was chromatographed on a silica gel column eluted with 25% acetone in hexane to afford 370 mg of a white foam (R$_f$ 0.09) which was identified by $^1$H NMR and mass spectrometry as 13-epi-avermectin B$_2$. Elemental analysis: calculated for C$_{48}$H$_{74}$O$_{15}$: C, 64.70; H, 8.47; found: C, 64.40; H, 8.47.

EXAMPLE 25

4″-acetylamino-4″-deoxy-13-epi-22,23-dihydro-avermectin B$_1$

Substitution of 5-O-t-butyldimethylsilyl-4″-acetylamino-4″-deoxy-13-epi-22,23-dihydro-avermectin B$_1$ for 4″,5,23-tris-O-t-butyldimethylsilyl-13-epi-avermectin B$_2$ in the deprotection procedure of Example 24 affords 4''-acetylamino-4''-deoxy 13-epi-22,23-dihydro-avermectin $B_1$ (separable mixture of isomers at C-4'') which is identified by $^1H$ NMR and mass spectrometry.

EXAMPLE 26

4''-acetylamino-4''-deoxy-13-epi-4''-deoxy-avermectin $B_1$

Substitution of 5-O-t-butyldimethylsilyl-4''-acetylamino-4''-deoxy-13-epi-avermectin $B_1$ for 4'',5,23-tris-O-t-butyldimethylsilyl-13-epi-avermectin $B_2$ in the deprotection procedure of Example 24 affords 4''-acetylamino-4''-deoxy-13-epi-avermectin $B_1$ (separable mixture of isomers at C-4'') which is identified by $^1H$ NMR and mass spectrometry.

EXAMPLE 27

13-epi-avermectin $B_1$

Substitution of 4'',5-bis-O-t-butyldimethylsilyl-13-epi-avermectin $B_1$ for 4'',5,23-tris-O-t-butyldimethylsilyl-13-epi-avermectin $B_2$ in the deprotection procedure of Example 24 affords 13-epi-avermectin $B_1$ which is identified by $^1H$ NMR and mass spectrometry.

EXAMPLE 28

13-epi-avermectin $A_1$

Substitution of 4''-O-t-butyldimethylsilyl-13-epi-avermectin $A_1$ for 4'',5,23-tris-O-t-butyldimethylsilyl-13-epi-avermectin $B_2$ in the deprotection procedure of Example 24 affords 13-epi-avermectin $A_1$ which is identified by $^1H$ NMR and mass spectrometry.

EXAMPLE 29

5-O-t-butyldimethylsilyl-13-epi-avermectin $B_1$ tert-Butyldimethylsilyl chloride (22 mg) is added to a solution of 13-epi-avermectin $B_1$ (100 mg) and imidazole (24 mg) in 1.5 ml of dry dimethylformamide and the solution is stirred at room temperature for 24 hours. The reaction mixture is partitioned between ether (15 ml) and water (15 ml). the aqueous layer is extracted with ether (20 ml) and the combined organic layers are dried with magnesium sulfate, filtered and evaporated. The crude product is chromatographed on a 1 mm silica gel plate eluted with 25% acetone in hexane to afford 5-O-t-butyldimethylsilyl-13-epi-avermectin $B_1$ which is identified by $^1H$ NMR and mass spectrometry.

EXAMPLE 30

5-O-t-butyldimethylsilyl-4''-amino-4''-deoxy-13-epi-avermectin $B_1$

Oxalyl chloride (0.022 ml) is added to a cold ($-78°$ C.) solution of DMSO (0.042 ml) in 2 ml of dry dichloromethane and the resulting solution is stirred for 20 minutes at $-78°$ C. A solution of 5-O-t-butyldimethylsilyl-13-epi-avermectin $B_1$ (80 mg) in 2 ml of dry dichloromethane is then added. The resulting mixture is stirred at $-78°$ C. for 1 hour then triethylamine (0.115 ml) is added and the cold bath is removed. The mixture is allowed to warm to room temperature and is stirred at room temperature for 1 hour. The mixture is diluted with dichloromethane (3 ml) then water (5 ml) is added and the layers are separated. The aqueous layer is extracted with dichloromethane ($3 \times 5$ ml) and the combined organic layers are dried over $MgSO_4$, filtered and evaporated. This crude oxidation product (5-O-t-butyldimethylsilyl-4''-oxo-13-epi-avermectin $B_1$) is dissolved in 2 ml of dry methanol then 3A molecular sieves are added followed by ammonium acetate (62 mg). The mixture is stirred at room temperature for 30 minutes then sodium cyanoborohydride (18 mg) is added in two portions (ca. 10 minutes apart). The mixture is stirred at room temperature for 2 hours then centrifuged. The supernatant is decanted and the solid residue is washed with dichloromethane ($2 \times 3$ ml). The combined supernatants are added to 3 ml of 5% aqueous $NaHCO_3$. The layers are separated and the aqueous layer is extracted with dichloromethane ($2 \times 3$ ml). The combined organic layers are dried over $MgSO_4$, filtered and evaporated. The residue is chromatographed on a silica gel column to afford 5-O-t-butyldimethylsilyl-4''-amino-4''-deoxy-13-epi-avermectin $B_1$ (separable mixture of isomers at C-4'') which is identified by $^1H$ NMR and mass spectrometry.

EXAMPLE 31

4''-amino-4''-deoxy-13-epi-avermectin $B_1$

Substitution of 5-O-t-butyldimethylsilyl-4''-amino-4''-deoxy-13-epi-avermectin $B_1$ for 4'',5,23-tris-O-t-butyldimethylsilyl-13-epi-avermectin $B_2$ in the deprotection procedure of Example 24 affords 4''-amino-4''-deoxy-13-epi-avermectin $B_1$ (separable mixture of isomers at C-4'') which is identified by $^1H$ NMR and mass spectrometry.

EXAMPLE 32

5-O-t-butyldimethylsilyl-4''-methylamino-4''-deoxy-13-epi-avermectin $B_1$

Substitution of methylamine hydrochloride for ammonium acetate in the reductive amination procedure of Example 30 affords 5-O-t-butyldimethylsilyl-4''-methylamino-4''-deoxy-13-epi-avermectin $B_1$ (separable mixture of isomers at C-4'') which is identified by $^1H$ NMR and mass spectrometry.

EXAMPLE 33

4''-methylamino-4''-deoxy-13-epi-avermectin $B_1$

Substitution of 5-O-t-butyldimethylsilyl-4''-methylamino-4''-deoxy-13-epi-avermectin $B_1$ for 4'',5,23-tris-O-t-butyldimethylsilyl-13-epi-avermectin $B_2$ in the deprotection procedure of Example 24 affords 4''-methylamino-4''-deoxy-13-epi-avermectin $B_1$ (separable mixture of isomers at C-4'') which is identified by $^1H$ NMR and mass spectrometry.

EXAMPLE 34

5-oxo-13-epi-avermectin $B_2$

Manganese dioxide (65 mg) is added to a solution of 100 mg of 13-epi-avermectin $B_2$ in 5 ml of dry benzene. The resulting mixture is stirred at $35°$ C. until complete by analytical thin layer chromatography. The mixture is partitioned between water (5 ml) and ether (5 ml) and the aqueous layer extracted with ether ($3 \times 5$ ml). The combined organic layers are dried over $MgSO_4$, filtered and evaporated. The crude product is chromatographed on a silica gel plate to afford 5-oxo-13-epi-avermectin $B_2$ which is identified by $^1H$ NMR and mass spectrometry.

EXAMPLE 35

13-epi-avermectin $B_2$-5-oxime

Hydroxylamine hydrochloride (50 mg) is added to a solution of 5-oxo-13-epi-avermectin $B_2$ (75 mg) in 3 ml of dry pyridine. The solution is stirred at room temperature until complete by analytical thin layer chromatography. The mixture is partitioned between water (7 ml) and ether (7 ml) and the aqueous layer extracted with ether (3×5 ml). The combined organic layers are dried over $MgSO_4$, filtered and evaporated. The crude product is chromatographed on a silica gel plate to afford 13-epi-avermectin $B_2$-5-oxime which is identified by $^1H$ NMR and mass spectrometry.

What is claimed is:

1. A compound having the formula:

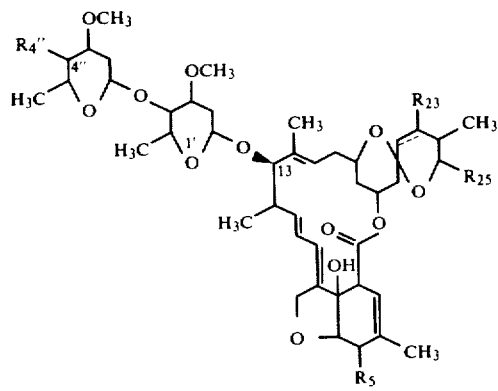

wherein:
$R_{4''}$ = OH, $NH_2$, NH-loweralkyl, NH-loweralkyanol;
$R_5$ = OH, oxime, $OCH_3$;
$R_{23}$ = H, OH; (provided $R_{23}$ is not OH if the broken line indicates a double bond);
$R_{25}$ = loweralkyl; and
the broken line indicates a single or double bond at the 22,23 position, provided that the broken line is not a single bond if $R_{4''}$ = OH and $R_{23}$ = H.

2. The compound of claim 1 wherein
$R_{4''}$ = OH, $NH_2$, NH-loweralkyl, NH-loweralkyanoyl;
$R_5$ = OH;
$R_{23}$ = H, OH;
$R_{25}$ = isopropyl or secbutyl; and
the broken line indicates a single or double bond.

3. The compound of claim 2 wherein
$R_{4''}$ = OH, NH-methyl, NH-acetyl;
$R_5$ = OH;
$R_{23}$ = H, OH; and
the broken line indicates a single or double bond.

4. The compound of claim 3 wherein
$R_{4''}$ = OH, NH-acetyl;
$R_{23}$ = H, OH; and
the broken line indicates a single or double bond.

5. The compound of claim 1 which is 13-epi-avermectin $B_1$.

6. The compound of claim 1 which is 13-epi-avermectin $B_2$.

7. The compound of claim 1 which is 13-epi-avermectin $A_1$.

8. The compound of claim 1 which is 4''-epi-amino-4''-deoxy-13-epi-avermectin $B_2$.

9. The compound of claim 1 which is 4''-epi-methylamino-4''-deoxy-13-epi-avermectin $B_1$.

10. The compound of claim 1 which is 4''-epi-methylamino-4''-deoxy-13-epi-avermectin $B_2$.

11. The compound of claim 1 which is 4''-epi-acetylamino-4''-deoxy-13-epi-avermectin $B_1$.

12. The compound of claim 1 which is 4''-epi-acetylamino-4''-deoxy-13-epi-22,23-dihydro-avermectin $B_1$.

13. The compound of claim 1 which is 4''-acetylamino-4''-deoxy-13-avermectin $B_2$.

14. The compound of claim 1 which is 4''-acetylamino-4''-deoxy-13-epi-avermectin $B_2$.

15. The compound of claim 1 which is 13-epi-avermectin $B_2$-5-oxime.

16. The compound of claim 1 which is 13-epi-avermectin $B_1$-5-oxime.

17. A method for the treatment and/or prevention of parasitic infections in animals which comprises treating such animals with an effective amount of a compound of claim 1.

18. A method for the treatment of pests of plants which comprises treating said plants or the soil in which they grow with an effective amount of a compound of claim 1.

19. A composition useful for the treatment and/or prevention of parasitic infections of animals which is comprised of an inert carrier and a compound of claim 1.

20. A composition useful for the treatment of pests of plants which is comprised of an inert carrier and a compound of claim 1.

* * * * *